(12) United States Patent
Ebensen et al.

(10) Patent No.: US 8,119,689 B2
(45) Date of Patent: Feb. 21, 2012

(54) ADJUVANTS ON THE BASIS OF BISACYLOXYPROPYLCYSTENE CONJUGATES AND DERIVATIVES AND THEIR USES IN PHARMACEUTICAL COMPOSITIONS

(75) Inventors: Thomas Ebensen, Hannover (DE); Michael Morr, Wolfenbittel (DE); Carlos Guzman, Wolfenbittel (DE)

(73) Assignee: Helmholtz-Zentrum Fuer Infektionsforschung GmbH, Braunschweig (DE)

( * ) Notice: Subject to any disclaimer, the term of this patent is extended or adjusted under 35 U.S.C. 154(b) by 563 days.

(21) Appl. No.: 12/093,865

(22) PCT Filed: Nov. 22, 2006

(86) PCT No.: PCT/EP2006/011182
§ 371 (c)(1),
(2), (4) Date: Sep. 24, 2008

(87) PCT Pub. No.: WO2007/059931
PCT Pub. Date: May 31, 2007

(65) Prior Publication Data
US 2009/0017106 A1    Jan. 15, 2009

(30) Foreign Application Priority Data
Nov. 22, 2005   (EP) .................................. 05025431

(51) Int. Cl.
| | | |
|---|---|---|
| *A01N 37/02* | (2006.01) | |
| *A01N 37/06* | (2006.01) | |
| *A61K 31/225* | (2006.01) | |
| *A61K 51/00* | (2006.01) | |
| *A61K 45/00* | (2006.01) | |
| *C07C 321/00* | (2006.01) | |
| *C07C 323/00* | (2006.01) | |
| *C07C 381/00* | (2006.01) | |
| *A61M 36/14* | (2006.01) | |

(52) U.S. Cl. ...... 514/547; 560/153; 424/1.65; 424/1.11; 424/280.1

(58) Field of Classification Search .................. None
See application file for complete search history.

(56) References Cited

U.S. PATENT DOCUMENTS

| | | | |
|---|---|---|---|
| 7,316,996 B2 * | 1/2008 | Muhlradt et al. ............ 514/21.9 |
| 2007/0060497 A1 * | 3/2007 | Krahmer et al. .................. 514/2 |

FOREIGN PATENT DOCUMENTS

| | | |
|---|---|---|
| WO | WO 2004/009125 A | 1/2004 |
| WO | WO 2004/108634 A | 12/2004 |

OTHER PUBLICATIONS

J. Milton Harris et al.; "Effect of Pegylation of Pharmaceuticals"; Nature Reviews, vol. 2, Mar. 2003, pp. 214-221.

* cited by examiner

Primary Examiner — Robert M Kelly
(74) Attorney, Agent, or Firm — Whitham Curtis Christofferson & Cook, PC

(57) ABSTRACT

Bisacyloxycysteine type conjugates have been found to be useful as adjuvants and/or immunomodulators for prophylactic and/or therapeutic vaccination in the treatment of infectious diseases, inflammatory diseases, autoimmune diseases, tumors, and allergies, as well as in the control of fertility in human or animal populations. The compounds can be administered by system or mucosal routes and are particularly useful as mucosal adjuvants. These compounds can function as active ingredients in pharmaceutical compositions.

29 Claims, 26 Drawing Sheets

BPPcysGlyc4armPEG

ADJUVANTS ON THE BASIS OF BISACYLOXYPROPYLCYSTENE CONJUGATES AND DERIVATIVES AND THEIR USES IN PHARMACEUTICAL COMPOSITIONS

FIELD OF THE PRESENT INVENTION

The present invention relates to new adjuvants of the Bisacyloxypropylcysteine type and the uses in pharmaceutical compositions, like in vaccines. In particular, the present invention provides new compounds useful as adjuvants and/or immunomodulators for prophylactic and/or therapeutic vaccination in the treatment of infectious diseases, inflammatory diseases, autoimmune diseases, tumours, allergies as well as for the control of fertility in human or animal populations. The compounds are particularly useful not only as systemic, but preferably as mucosal adjuvants. In addition, the invention relates to its uses as active ingredients in pharmaceutical compositions.

BACKGROUND OF THE INVENTION

Infectious diseases are the major cause of morbidity and mortality, accounting for a third of the deaths which occur in the world each year. In addition, infectious agents are directly responsible for at least 15% of new cancers, and they also seem to be involved in the pathophysiology of several chronic diseases (e.g. inflammatory, vascular and degenerative diseases). Traditional infectious diseases are also highly expensive in terms of health-associated costs of infected patients and loss in productivity at work.

The main strategies used to prevent infectious diseases are therapy and prophylaxis. Vaccination has become the most cost-effective measure to prevent infections. However, there are still many diseases for which vaccines are not yet available or the available vaccines are not completely satisfactory due to low efficacy, high reactogenicity, poor stability and/or high costs. Thus, there is still an urgent need for both new and improved vaccines.

Despite the fact that vaccines have traditionally been used for the prophylaxis of infectious diseases, recent findings suggest that they are also a powerful tool for the immunotherapy of transmissible diseases (e.g. viral hepatitis, *Helicobacter pylori* infections, herpes virus infections, etc.). In addition, vaccines can be used for the immune-therapy or immune-prophylaxis of autoimmune diseases, inflammatory diseases, tumours, allergies and for the control of fertility in human and/or animal populations. In particular, the last application seems to require the elicitation of efficient mucosal responses at the level of the reproductive tract.

Most infectious diseases are either restricted to the mucosal membranes or the etiologic agents need to transit the mucosa during the early steps of the infection. Therefore, it is desirable to obtain not only a systemic, but also a local mucosal immune response as a result of vaccination, thereby blocking both infection (i.e. colonization) and disease development. This may result in a more efficient protection against infection, facilitating also the eradication of diseases for which humans are the only reservoirs (i.e. blocking transmission to susceptible hosts). Parenterally-administered vaccines mainly stimulate systemic responses, whereas vaccines administered by a mucosal route mimic the immune response elicited by natural infections and can lead to efficient mucosal and systemic responses. Due to the apparent compartmentalization of the systemic and mucosal immune system, parenterally administered vaccines are less effective in protecting against mucosal pathogens (McGhee, J. R., Mestecky, J., Dertzbaugh, M. T., Eldridge, J. H., Hirasawa, M. and Kiyono, H. (1992) The mucosal immune system: from fundamental concepts to vaccine development. Vaccine 10, 75-88). Thus, administration of immunogens through the mucosal route is required to achieve full protection. However, most of the available vaccines are administered through the parenteral route, thereby, eliciting a systemic immunity in the individual.

The administration of vaccines via the mucosal route offers several advantages over parenteral vaccination. These advantages include an ease of administration, the possibility of self-administration (e.g. by intranasal, rectal or oral application), the elimination of the chance of unwanted cross-infection due to the use of infected needles or non-sterile working, lower rates of side effects, higher acceptance by the public, better compliance of vaccination protocols (i.e. increment in the overall efficacy), simpler administration logistics and lower delivery costs, being particularly suitable for mass immunization programmes. However, the compartmentalisation at the level of the mucosal immune system has to be taken into consideration. In fact, immune responses which can be observed following intra-nasal vaccination may not necessarily occur after oral or intra-rectal immunisation. For example, oral vaccination may not stimulate efficient responses in the genitourinary and/or respiratory tracts.

Unfortunately, the delivery of antigens by the mucosal route is associated with a major problem, namely that antigens delivered by this route are generally poorly immunogenic. This is the result of different mechanisms, such as (i) accelerated antigen elimination by the non specific host clearance mechanisms (e.g. ciliar activity, peristaltism), (ii) antigen degradation by local enzymes, (iii) antigen alteration and/or structural modification as a result of extreme pH (e.g. acidic in the stomach, alkaline in the intestine), (iv) poor antigen penetration through the mucosa, (v) limited access of vaccine antigens to antigen presenting cells, and (vi) local peripheral tolerance.

To overcome these problems, different strategies have been used, such as antigen entrapment or association with physical or biological particles (e.g. microparticles, nanoparticles, bacterial ghosts), the use of virosomes or viral-like-particles, the use of liposomes or ISCOMS, the use of transgenic plants, antigen production by attenuated viral or bacterial carriers acting either as conventional vectors or as carriers for nucleic acid vaccines and/or their administration with mucosal adjuvants. However, despite the heavy body of experimental evidence generated in pre-clinical studies during the last years, almost no candidates have been transferred to the vaccine development pipeline.

The use of optimal adjuvants plays a crucial role in vaccination. Antigens administered without adjuvant only rarely mediate an adequate immune response. In addition, not only the strength but also the quality of the elicited immune response matters. Stimulation of an incorrect immunization pattern may lead to immunopathological reactions and exacerbation of the symptoms of infection. In this context, the adjuvant can help to assist the desired immune response. In other words, an adjuvant can modulate the immune response or redirect the immune response to balance the immune response in the desired direction.

Substances referred to as "adjuvants" are those which are added and/or co-formulated in an immunization to the actual antigen (i.e. the substance which provokes the desired immune response) in order to enhance the humoral and/or cell-mediated immune response ("Lexikon der Biochemie und Molekularbiologie", 1. Band, Spektrum, Akademischer Verlag 1995). That is, adjuvants are compounds having immunopotentiating properties, in particular, when co-administered with antigens. The use of many adjuvants is based solely on experience, and the effect can neither be accurately explained nor predicted. The following groups of adjuvants are traditionally used in particular: aluminium hydroxide, emulsions of mineral oils, saponins, detergents, silicon compounds, thiourea, endotoxins of gram-negative bacteria, exotoxins of gram-positive bacteria, killed or attenuated living bacteria or parts thereof.

An overview over the presently known mucosal adjuvants and delivery systems, e.g. the above mentioned particles, ICOMS, liposomes and viral-like particles, for protein-DNA- and RNA-based vaccines is given in Vajdy et al., Immunol. Cell Biol., 2004, 82, 617-627. Therein the currently available approaches in immunopentiation of mucosal vaccines are discussed.

That is, various mucosal adjuvants have been described which should serve as an alternative for the adjuvants useful for systemic administration, e.g. see Vajdy et al., supra. These mucosal adjuvants include heat labile enterotoxin and detoxified mutants thereof. In particular, genetically detoxified mutants of heat labile enterotoxin of *E. coli* have been developed as useful mucosal adjuvants. Moreover, cholera toxin of *vibrio cholera* is known as an adjuvant useful for mucosal vaccination. Further, the application of unmethylated CpG dinucleotides has been described. It was shown that CpG can bias the immune response towards a Th1 response and can modulate pre-existing immune responses. Saponins are also described as immunomodulatory substances, predominantly via the induction of specific cytokines which then modulate and/or activate the immune response.

Unfortunately, most of the compounds described above being useful as mucosal adjuvants are not utilisable due to their intrinsic toxicity, e.g. retrograde homing to neuronal tissues of bacterial toxoids and/or toxins at/in the derivatives after nasal vaccination.

In addition, as adjuvants which may be useful in mucosal vaccination the following have been described:

The MALP-2 molecule and derivatives thereof, like Bisaxcyloxypropylcysteine-conjugates, e.g. a Bispalmitoyloxypropylcysteine-PEG molecule are known to represent potent stimulants for macrophages. The usefulness of MALP-2 as an adjuvant was shown previously, see e.g. WO2004/009125 and WO2003/084568. In particular, it was demonstrated that MALP-2 can act as an effective adjuvant enhancing the immune response, e.g. fostering an enhanced expression of antigen-specific IgA antibodies.

Furthermore, it was shown that MALP-2 can activate dendritic cells and B-cells, both play an important rule in the induction of a specific humoral immune response. In addition preliminary studies demonstrate that a combination for biologically active HIV-1 tat protein and synthetic MALP-2 may be a promising vaccine with the MALP-2 component as an effective adjuvant e.g. via the mucosal route.

However, the Bisacyloxypropylcysteine-conjugates having one polyalkylene unit as described in WO 2004/009125, BPPcysPEG or BPPcysMPEG are obtainable as polydisperse molecules being different in size of the polyalkylene unit and, thus, having a wide range of molecular size only. Hence, it is not possible to purify conjugates of a single size by known and industrially applicable techniques.

There is still a need to provide adjuvants being more stable and active, i.e. having an improved bioavailability, thus, allowing reducing the dosage of the adjuvants in the vaccines. Furthermore, there is still a need to provide compounds having improved solubility in hydrophilic solvents and being improved in their dwell time in the body, in particular, being more stable against metabolism and excretion. Furthermore, new compounds are required having an improved shelf life.

Thus, none of these previously described mucosal adjuvants have been approved yet, but, today, only two systemic adjuvants received approval to be administered to humans and, hence, are used for the preparation of human vaccines. These adjuvants are Alum and MF59. However, both are not effective as mucosal adjuvants.

There has been an intensive search in recent years for novel adjuvants, including those for the mucosal administration route. Only a few substances have been found to be able to enhance mucosal responses. Among these, some act as carriers to which the antigens must be bound or fused thereto. Far fewer universally employable "true" adjuvants which are admixed to the antigens have been found, as outlined above.

Hence, there is still a need in the prior art to provide new compounds useful as adjuvants, particularly as mucosal adjuvants and/or as vaccines. In particular, there is a need for mucosal adjuvants which can elicit a strong immune response which represent a balanced or adjusted immune response involving both humoral and cellular components, thus, allowing effective prophylaxis or treatment of various diseases and conditions, specifically of infectious diseases or cancer. Furthermore, the bioavailability of said adjuvants should be good with excellent stability and activity, thus, allowing to reduce the dosage and to increase biosafety of the adjuvants.

Thus, the object of the present invention is the provision of mucosal adjuvants which can elicit and/or enhance and/or modulate (pre-existing) immune response in an individual or subject. In particular, the invention is based on the object of developing a range of novel, highly active adjuvants, particularly mucosal adjuvants which are non-toxic for humans and which can be employed with a wide variety of active ingredients to be assisted in conventional or novel vaccines such as, in particular, prophylactic or therapeutic vaccines, including cancer and DNA vaccines.

DESCRIPTION OF THE INVENTION

This technical problem is solved by the provision of the embodiments as characterized in the claims.

The present invention is generally concerned with the provision of new conjugates or salts or solvates thereof, useful as immunomodulatory compounds, in particular, as adjuvants, preferably as mucosal adjuvants. Furthermore, the present invention relates to new pharmaceuticals comprising the conjugates as described herein with pharmaceutically acceptable carrier(s), optionally together with additional active ingredients.

That is, the present invention relates to the provision of the use of specific compounds or conjugates useful as adjuvants and/or immunomodulators in therapeutic or prophylactic vaccination. Said compounds and conjugates are useful as systemic and are particularly useful as mucosal adjuvants being applied via the mucosa of the individual.

The present inventors now found that specific forms of Bisacyloxypropylcysteine-conjugates are particularly useful as adjuvants in vaccines for therapeutic or prophylactic vaccination. In particular, compounds as described herein demonstrate the applicability as parenteral adjuvants and, in particular, as mucosal adjuvants at low doses.

As used herein, the term "adjuvant" means substances which are added and/or co-formulated in an immunization to the active antigen, i.e. the substance which provokes the desired immune response, in order to enhance or elicit or modulate the humoral and/or cell-mediated (cellular)

immune response against the active antigen. Preferably, the adjuvant according to the present invention is also able to enhance or elicit the innate immune response.

The term "therapy" or "treatment" refers to a process that is intended to produce a beneficial change in the condition of an individual like a mammal, e.g., a human, often referred to as a patient, or animal. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy usually encompasses the administration of a drug, among others.

As used herein, the term "delivery system" refers to a system that is more inert and has less immunomodulatory effects than adjuvants and which can protect and deliver the vaccine to the site of interest through the site of administration. In particular, the delivery system allows for more efficient presentation of the antigen to the immune system. Examples of delivery systems are virus or virus-like particle, ISCOM, nanoparticles, microparticles, liposomes, virosomes, polyoma-like particles, attenuated vaccines and virus-like particles.

As used herein, the term "pegylated" refers to the conjugation of a compound moiety with conjugate moiety(ies) containing at least two polyalkylene unit. In particular, the term pegylated refers to the conjugation of the compound moiety with a conjugate moiety having at least two polyethylene glycol units. The term "pegylated" does not include forms having a linear pegylation of the bisacyloxypropylcysteine residue.

As used herein, the term "mucosal" refers to mucosal surface from the body such as the nasal, oral, gastro-enteric, rectal, urinary, conjunctial, glandular, e.g. mammary gland, epithelial mucous.

As used herein, the term "conjugate" refers to compounds comprising a conjugate moiety and a compound moiety. The compound moiety is a bisacyloxypropylcysteine residue. The term "conjugate moiety" refers to a moiety which is linked to the bisacyloxypropylcysteine residue. The conjugate moiety aims to increase the applicability of the compounds disclosed herein.

As used herein, the term "antigenic structure" or "antigen" refers to a structure capable of causing a cellular or humoral immune response. The antigenic structure, also known as epitope is the part of the antigen, which is presented by the MHC or MHC like molecules. Further, the epitope or antigenic structure represents the part of an antigen recognized by antibodies directed against said antigen.

As used herein, the term "modulate an immune response" refers to any change of the present state of the immune response. The immune response may be modulated insofar that the response is elicited or a pre-existing immune response is enhanced or decreased. In addition, the immune response may be modulated by shifting the immune response from a more humoral to a more cellular immune response or vice versa. Further, the immune response may be modulated by switching or redirecting the response from a Th1 to Th2 or Th3 response or vice versa, in particular a balanced Th1/Th2 response. In addition, the modulation of the immune response may encompass the activation or enhancement of the innate immune response.

As used herein, the term "individual" or "subject" which is used herein interchangeably refers to an individual or a subject in need of a therapy or prophylaxis. Preferably, the subject or individual is a vertebrate, even more preferred a mammal, particularly preferred a human.

As used herein, the term "carrier" refers to a diluent, adjuvant, excipient, or vehicle.

In a first aspect, the present invention relates to the use of a Bisacyloxypropylcysteine-conjugate according to formula 1:

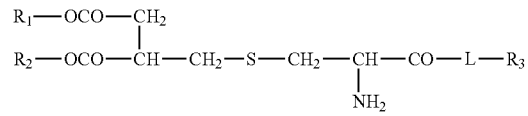

where $R_1$ and $R_2$ can be identical or different and are acyl moieties;

L is a linker moiety selected from the group of NH, O, S or OCO;

$R_3$ is a covalently linked conjugate moiety comprising at least two polyalkylene glycol units of the formula:

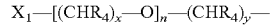

which may be identical or different;

where $X_1$ is hydrogen or a hydrocarbon which may contain heteroatom(s), e.g. a straight or branched $C_1$-$C_6$ alkyl group or a straight or branched $C_1$-$C_6$ alkoxy group;

$R_4$ is independently any one of hydrogen, OH, $C_1$-$C_6$ straight or branched alkyl group, $OR_5$ or CO—$R_6$;

$R_5$ is independently any one of hydrogen or $C_1$-$C_6$ straight or branched alkyl;

$R_6$ is independently any one of hydrogen, OH, $OR_5$ or $NR_7R_8$;

$R_7$ and $R_8$ are independently any one of hydrogen or hydrocarbon which may contain heteroatom(s) and which may form a ring;

n is an integer of 1 to 100;

x is independently an integer of 1 to 10;

y is an integer of 0 to 10 as adjuvant(s) for therapeutic or prophylactic vaccination.

In a second aspect, the present invention relates to a Bisacyloxycysteine-derivative according to formula (1) where $R_1$ and $R_2$ are defined as above, L is Amino-3'-deoxyadenosine, Amino-3'-deoxyguanosine, Amino-3'-deoxyinosine, or Amino-3'-deoxyxanthine and $R_3$ may be absent or may be covalently bonded with the purine residue, e.g. at position 6 of the purine ring and is defined as outlined above. Preferably, said derivative is S-[2,3-bis(palmitoyloxy)-(2S or 2R)-propyl]-L-cysteinylcarboxy-3'Amino-3'-deoxyadenosine (BPP-cysAda). Alternatively, the Bisacyloxycysteine-derivative according to formula (1) may be further succinylated.

Preferably, the conjugate is characterized in that the residues $R_1$ and $R_2$, which may be identical or different, are independently a $C_7$-$C_{25}$ acyl group, preferably $C_8$-$C_{22}$-alkyl, -alkenyl, or alkynyl groups, and the unsaturated positions are preferably in the cis configuration, the alkyl-, alkenyl-, and alkynyl residues may be linear, branched or cyclic residues which may be substituted.

With the term "which may be substituted" is meant a substitution with a straight or branched $C_1$-$C_6$ alkyl group or a straight or branched $C_1$-$C_6$ alkoxy group and/or with a halogen, hydroxyl group or carboxyl group.

The conjugate moiety of the conjugate according to the present invention is a covalently bonded, physiologically tolerated conjugate moiety, which is suitable for converting the bisacyloxypropylcysteine residue into a more water-soluble form. The conjugate moiety is characterized in that is provides good solubility in hydrophilic solvents, like water, and is not immunogenic. Further, the conjugate moiety provides considerably greater protease stability, a significant decrease in immunogenicity and a perceptible delaying of renal excretion. The new pegylated structure covers the drug molecule almost completely, thus shielding it effectively against premature degradation by antibodies and endogenous enzymes. Furthermore, with the help of this masking reagent, the drug can withstand attacks by the immune system and enzymatic degradation processes, can reach its destination unimpeded and exerts its therapeutic effect efficiently. Thus, the amount of adjuvant or active ingredient necessary to achieve the desired effects can be significantly reduced while improving the bioavailability.

In particular, the conjugate moiety of the conjugate claimed herein, is a conjugate moiety containing at least two polyalkylene glycol units which are not in a row but be present in a branched structure. Branched structure means that the units are directly or indirectly covalently linked via a branching molecule and said branching molecule is directly or indirectly linked with the bisacyloxypropylcysteine residue of the formula:

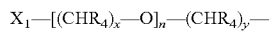

which may be identical or different;
where
$X_1$ is hydrogen or a hydrocarbon which may contain heteroatom(s), like a straight or branched $C_1$-$C_6$ alkyl group or a straight or branched alkoy group;
$R_4$ is independently any one of hydrogen, OH, straight or branched $C_1$-$C_6$ alkyl group, $OR_5$ or $CO$—$R_6$;
$R_5$ is independently any one of hydrogen or straight or branched $C_1$-$C_6$ alkyl;
$R_6$ is independently any one of hydrogen, OH, $OR_5$ or $NR_7R_8$;
$R_7$ and $R_8$ are independently any one of hydrogen or hydrocarbon which may contain heteroatom(s) and which may form a ring;
n is an integer of 1 to 100;
x is independently an integer of 1 to 10;
y is an integer of 0 to 10
Preferably, n is an integer of 2 to 50, like 2 to 10, in particular 3 to 5.
y is preferred an integer of 1 to 5, in particular, 1 to 3, in another preferred embodiment, y is 0.
Preferably, x is an integer of 2, 3, or 4, in particular 2.
$X_1$ is preferentially $OR_9$, $N(R_9)_2$, $SR_9$ or $COOR_9$, wherein each $R_9$ is individually hydrogen, benzyl or straight or branched $C_1$-$C_6$ alkyl, preferably a straight or branched $C_1$-$C_6$ alkoxy group, like a methoxy, ethoxy or propoxy group.
$R_4$ is preferably a hydrogen atom.
Thus, the polyalkylene glycol unit mentioned above may preferably contain at least two subunits of ethylene glycol, propylene glycol or butylene glycol or combinations thereof. The chain length of each of the polyalkylene glycol units may be in the range of 1 to 100 subunits, preferably, 2 to 50 subunits, like 2 to 10 subunits, particularly in the range of 3 to 5 subunits.

The polyalkylene units present in the conjugate according to the present invention do not have a linear conjugate moiety but the at least two units are present in a branched form, e.g. shown in FIGS. 10 and 11.

Particularly preferred the polyalkylene glycol subunit is a methoxypolyalkyleneglycol-carbonyl-residue wherein the alkylene moiety is an ethylene or propylene moiety.

Hence, the pegylated form as defined herein allows increasing the solubility in hydrophilic solvents and hydrophilic environment. Furthermore, the conjugate moiety allows protecting the compound moiety, i.e. the active mucosal adjuvant moiety, against enzymatic degradation, structural modification due to change of the pH, mechanical removal, etc. Thus, primarily the stability of the compound is increased. Another beneficial effect of conjugation is to increase the retention time in the individual, e.g. to delay the renal excretion, while being well-tolerated, e.g. being non immunogenic, by said organism. Thus, the conjugate according to the present invention display an improved bioavailability while allowing reduction of the dosage necessary to elicit the desired effect.

In addition, the conjugates or derivatives according to the present invention maintain their activity even after storage for 2 month at room temperature, as shown in FIG. 12.

Specifically, the conjugate moiety comprises at least four chains having polyalkylene glycol units. The conjugate may be a branched compound wherein each arm contains a polyalkylene glycol unit. Particularly preferred are conjugate moieties wherein the polyalkylene glycol unit is a polyethylene, polypropylene or polybutylene glycol unit.

In a particularly preferred embodiment, the compound moiety being covalently linked with the conjugate moiety is a branched moiety wherein at least two arms containing polyethylene glycol units having 3 to 5 ethylene glycol subunits and a methoxy group at the free end of the polyethylene group. In particular, the branched moiety comprises 4 or 6 or 8 arms each having 3 ethylene glycol subunits and a methoxy group at the free end of the polyethylene group.

In particular, the conjugate is characterized in that the conjugate moiety is 4armPEG ((S)-10-Amino-6,9,13,16-tetraoxo-N,N',8,14-tetrakis(3,6,9,12-tetraoxamidec-1-yl)-5,8,14,17-tetraazahenicosane-1,21-diamide), 6armPEG or 8armPEG as described in WO 2004108634 which is incorporated herein in its entirety. Other suitable conjugate moiety comprising at least two polyethylene unit are obtainable e.g. from celares GmbH, Berlin, see http://www.celares.com or Nektar Therapeutics, www.nektar.com/peg and specific examples are shown in FIG. 9.

A particularly preferred embodiment is the compound of formula (2) as shown in FIG. 11.

The conjugates described herein may be in the form of pharmaceutically acceptable non-toxic salts thereof. Salts include acid added salts, such as salts with inorganic acids (e.g. hydrochloric acid, sulphuric acid, nitric acid and phosphoric acid) or with organic acids (e.g. acetic acid, propionic acid, maleic acid, olec acid, palmitic acid, citric acid, succinic acid, tartaric acid, fumaric acid, glutamic acid, panthothenic acid, laurylsulfonic acid, methanesulfonic acid and phthalic acid).

The conjugates may be in the form of solvates thereof (e.g., hydrates).

In addition, the conjugates may form salts with cationic ions, like metallic ions, in particular alkali or alkaline earth metal ions, or NH4+.

Preferably the conjugate according to the present invention is a S-[2,3-bis(acyloxy)-(2S)-propyl]-L-cysteinylcarboxy-conjugate, preferably, a S-[2,3-bis(palmitoyloxy)-(2S)-propyl]-L-cysteinylcarboxy-conjugate.

In another embodiment the conjugate is a S-[2,3-bis(acyloxy)-(2R)-propyl]-L-cysteinylcarboxy-conjugate, preferably, a S-[2,3-bis(palmitoyloxy)-(2R)-propyl]-L-cysteinylcarboxy-conjugate.

The conjugates as described above can additionally used as an immunomodulator in a pharmaceutical composition for preventing or treating infectious diseases, cancers, tumours, autoimmune diseases or allergies, or chronic or acute inflammatory processes or to control fertility in human or animal populations.

The synthesis of conjugates may be conducted by methods known to the person in the art. For example, a hydroxyl group may be converted into a halogen residue, e.g. Cl, Br, I and this residue can react with modified conjugates having a free amino-group. For example, synthesis of pegylated conjugates are described in Veronese F. M., Biomaterials 22 (2001), 405-417 and Kodera Y., et al., Prog. Polym. Sci. (1998), 23, 1233-1271 which are incorporated herein by reference.

In a preferred embodiment, the conjugate(s) or salts or solvates thereof are useful as mucosal adjuvant(s), in particular, for intranasal, intra NALT, oral, intra-rectal, conjunctival, intra-vaginal, intrathecal, intrabronchial, intrapulmonary, or intra-urethral administration, administration into the milk ducts of the breast or by inhalation. Particularly preferred is the intranasal administration or the administration by inhalation using suitable aerosol formulations. Aerosol formulations useful for administration of vaccines are known in the art.

The conjugates or salts or solvates thereof are also suitable as systemic adjuvant(s). Thus, the adjuvants described herein are also applicable as parenteral adjuvant(s), in particular, in subcutaneous, topical (transcutanous vaccination), intravenous, intradermal, topical or intramuscular administration.

The adjuvant of the invention can be linked by all methods known to the skilled person to the antigen or active molecule intended for the vaccination, be incorporated together with the latter in physical (e.g. microparticles, nanoparticles, liposomes, ISCOMS, polymers) or biological particles (bacteria, bacterial parts) or virosomes or be mixed with the antigen. For example, the adjuvant may be co-formulated or admixed with the antigen. For binding to carriers it is also possible to provide transport molecules or transport proteins as carriers.

The conjugate(s) or salts or solvates thereof is/are preferably present in a preparation with the active vaccination component (e.g. the antigen) which is suitable and provided for intranasal, intra-NALT (nasal associated lymphoid tissue), aerosolized, oral, intrarectal, conjunctival, intravaginal, intraurethral administration or for administration into the milk ducts of the breast. Particularly, the preparation is provided in formulation suitable to be taken up via the respiratory tract or the gastro-intestinal tract. Alternatively, the mucosal adjuvant of the invention can be present in a kit for co-administration with a vaccine by one of the aforementioned routes and be adapted therefore where appropriate. That is the vaccine may be administered simultaneously, sequentially or separately with the active vaccination component.

Thus, the conjugates according to the present invention direct the immune response towards a balanced Th1/Th2 immune response. Also, said conjugates may bias the immune response by enhancing the Th2 immune response.

In another embodiment, the present invention relates to methods of treating individuals afflicted with a disease or condition that can be treated by modulating the immune response comprising administering to said individual an effective amount of a pharmaceutical comprising the conjugates, salts and solvates thereof as defined herein as an adjuvant, particularly as a mucosal adjuvants together with an active vaccination component, and, optionally, a pharmaceutically acceptable carrier.

Preferably, the method relates to the treatment of individuals afflicted with an infectious disease wherein the infectious disease is produced by an infectious agent selected among those causing human or animal disease at the level of the respiratory tract, gastrointestinal tract, genitourinary tract, osteoarticular system, skin or mucosa.

The conjugates or salts or solvates thereof as defined herein are particular useful as mucosal adjuvants for activating or enhancing in vitro and/or in vivo the antigen presenting function of antigen presenting cells for a therapeutic or prophylactic intervention. That means, the adjuvants can stimulate macrophages, can stimulate or enhance the humoral immune response, e.g. enhancing or stimulating the production of antibodies. In addition, the adjuvants can also enhance or stimulate the cellular immune response, e.g. increasing the proliferation of T-cells. In addition, it is possible to use the adjuvant(s) for ex vivo stimulation in cell culture, e.g. for the production of dendritic cells, etc. These cells obtained by ex vivo stimulation may be used for autologous cell transfer in transplantation or as a cell based vaccine against diseases or conditions, like the diseases and conditions mentioned above, including cancer, autoimmune disease or allergies.

Furthermore, the conjugates according to the present invention are useful for targeting in vitro, ex vivo and/or in vivo cells expressing for example the Toll like receptor system, including but not limited to TLR1, TLR-2 and/or TLR-6 receptor for a prophylactic or therapeutic intervention in the subject. Preferably, the use of the conjugate according to the present invention allows improving the vaccine efficacy by targeting cells expressing the Toll 2 and/or Toll 6 receptor.

Thus, in case of the use of the conjugates or salts or solvates thereof as defined herein as an adjuvant, the pharmaceutical composition according to the present invention is preferably a vaccine, comprising said compounds or conjugates or salts or solvates thereof as pharmaceutically acceptable adjuvant(s) together with the active vaccination component (e.g. the antigen) and, optionally, a pharmaceutically acceptable carrier, diluent, preservative, adjuvant other than the adjuvant according to the present invention, immunomodulator or excipient.

The active vaccination component may be any component suitable to elicit, enhance or modulate an immune response in an individual. The active vaccination component is suitable particularly for intranasal, intra-NALT, oral, intra-rectal, conjunctival, intra-vaginal, aerosolized or intra-urethral administration, or administration into the milk ducts of the breast.

For example, the active vaccination component, the active ingredient of the pharmaceutical composition, comprises at least one or more different antigens in the form of peptides, proteins, polysaccharides, glycolipids or DNA encoding them or bacterial ghost, virosomes, or attenuated vaccines.

Preferentially, the antigen(s) are tumor antigen(s) or antigen(s) derived from infectious agents. The infectious agents include those agents which normally enters individual's organism by crossing the mucous membrane.

The pharmaceutical composition comprising adjuvant(s) according to the present invention, an active vaccination component, optionally additional carrier, diluent, preservative, adjuvant other than the adjuvant according to the present invention, immunomodulator or excipient may additionally contains components, like compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

However, the conjugates and salts and solvates thereof as defined herein for the use as adjuvants may also be a component of a pharmaceutical composition provided in a formulation suitable for parenteral administration, in particular, in subcutaneous, transcutaneous (topical vaccination), intravenous, intradermal or intramuscular administration.

Further, the compounds according to the present invention are useful in tumor therapy including the in vitro generation or in vitro priming of autologous cells for adoptive cell transfer in tumor therapy and transplantation. Moreover, the adjuvants are useful for the induction of cross-tolerance against microbial components, like endotoxins, to protect against septic shock or other severe forms of diseases induced by microbial components.

In addition, the compounds themselves as defined herein may display a pharmaceutical activity, e.g. are to be useful in the prophylaxis and treatment of various diseases and conditions, like cancer, infectious diseases, septic shock, chronic and inflammatory processes, autoimmune diseases, allergies, etc.

Hence, the conjugates or salts or solvates thereof are also useful for the preparation of a pharmaceutical to prevent or treat infectious diseases, septic shock, cancer, tumours, autoimmune diseases, allergies, or chronic or acute inflammatory processes.

The conjugates according to the present invention and salts or solvates thereof can be used as active ingredients in pharmaceuticals useful for the prevention or treatment of infectious diseases, septic shock, tumours, autoimmune diseases, allergies, or chronic or acute inflammatory processes. In particular, the conjugates or salts or solvates thereof are contained in pharmaceuticals useful for preventing or treating cancer and/or tumours, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, *helicobacter pylori*, herpes virus, etc.; bacterial infections, such as tuberculosis, leprosy and listeriosis, and parasitic infections such as malaria.

Thus, in a further aspect, the present invention relates to pharmaceutical compositions comprising conjugates or salts or solvates thereof as defined herein, in particular, conjugates containing at least one conjugate moiety comprising at least two polyalkylene glycol unit, as defined herein or salts or solvates thereof and, optionally, a pharmaceutically acceptable carrier. Such pharmaceutical compositions comprise a therapeutically effective amount of the conjugates and, optionally, a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin ($18^{th}$ ed., Mack Publishing Co., Easton, Pa. (1990)). Such compositions will contain a therapeutically effective amount of the aforementioned conjugates and salts or solvates thereof, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in a unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve an increase in the immunological responses to infection or a suppression of the responses to inflammatory processes.

In vitro assays may optionally be employed to help identifying optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The term "administered" means administration of a therapeutically effective dose of the aforementioned pharmaceutical composition comprising the conjugates and salts and solvates thereof as defined herein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In still another embodiment, the present invention relates to methods of treating individuals suffering from infectious diseases, septic shock, tumours, autoimmune diseases, allergies, or chronic or acute inflammatory processes comprising the step of administering to said individual an effective amount of a pharmaceutical comprising a conjugate or salts or solvates thereof as the active ingredient, and, optionally, a pharmaceutically acceptable carrier. In particular, the method is useful for preventing or treating cancer and/or tumours, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, *helicobacter pylori*, herpes virus, etc.; bacterial infections, such as tuberculosis, leprosy and listeriosis, and parasitic infections such as malaria.

Further, the pharmaceutical composition may contain additionally components, e.g. compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

In addition, the pharmaceutical composition described herein may be characterized in that the components of the pharmaceutical composition are associated and/or incorporated and/or coated to a physical particle, preferably microparticle, nanoparticle, liposome, ISCOM, copolymer and/or biological particle, preferably bacterial ghosts.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, transcutaneously (topical vaccination), intradermally, intravenously, intra-arterial, intranodal, intramedullary, intrathecal, intraventricular, intranasally, conjunctival, intrabronchial, transdermally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 1000 µg; however, doses below or above this exemplary range are envisioned, especially considering the aforementioned factors.

Moreover, the use of the conjugates having multiple polyalkylene units allows reducing the required amount of said conjugates per dosage to obtain effective immunomodulation or adjuvanticity in individuals. In particular, using conjugates having multiple polyalkylene units, like the molecule shown in FIG. 10, BPPcysGlyc4armPEG, it is possible to reduce the dosage of the adjuvants significantly when compared with BPPcysPEG.

In still another aspect, the present invention relates to the use of the conjugate(s). or salts or solvates thereof as defined herein in a pharmaceutical preparation to control fertility in human or animal populations.

Finally, the present invention relates to kits comprising the conjugates according to the present invention or salts or solvates thereof. In particular, the kit is useful for the preparation of pharmaceutical compositions. Optionally, the kit contains instructions for preparing the pharmaceutical composition.

In a preferred embodiment thereof, the kit contains the conjugates according to the present invention or salts or solvates thereof as an adjuvant and an antigen comprising an antigenic structure and, optionally, a pharmaceutically acceptable carrier, diluent, preservative, adjuvants other than the conjugates according to the present invention, immunomodulators or excipient and instructions for preparing a vaccine.

These and other embodiments are disclosed and encompassed by the claims and the description and examples of the present invention. Further literature concerning any one of the methods, uses and compounds to be employed in accordance with the present invention may be retrieved from public libraries, using for example electronic devices. For example the public database "Medline" may be utilized which is available on the Internet. Further databases and addresses are known to the person skilled in the art. An overview of patent information in biotechnology and a survey of relevant sources of patent information useful for retrospective searching and for current awareness is given in Berks, TIBTECH 12 (1994), 352-364

BRIEF DESCRIPTION OF THE FIGURES

FIG. 1.

FIG. 2 illustrates the cellular responses of restimulated spleen cells using different concentrations of BPPcysGlyc4armPEG or BPPcysAda as adjuvant. T cell proliferative responses of spleen cells from Balb/c mice were restimulated in vitro during 4 days in the presence of different concentrations up to 40 µg/ml of soluble BPPcysGlyc4armPEG or up to 20 µg/ml of BPPcysAda. Results are expressed as counts per minute (A) and (C) and stimulation indexes (cpm samples/cpm in control non stimulated cells) (B).

FIG. 3 demonstrates the cellular responses stimulated following vaccination using different concentrations of BPPcysGlyc4armPEG as adjuvant. β-galactosidase-specific T cell proliferative responses of spleen cells from mice immunized by the i.p. or i.n. routes with either 1-galactosidase (30 µg/dose) alone or β-galactosidase mixed with different doses of BPPcysGlyc4armPEG or BPPcysPEG on days 0, 14 and 28. At day 38 post primary immunisation animals were sacrificed, and spleen cells were re-stimulated in vitro during 4 days in the presence of different concentrations of soluble β-galactosidase. Results are expressed as thymidine incorporation and as stimulation indexes (cpm samples/cpm in control non stimulated cells) (A) after i.n. administration or as thymidine incorporation and as stimulation indexes (cpm samples/cpm in control non stimulated cells) (B) after parenteral administration. (C) shows the stimulation index for BPPcysAda FIG. 4 shows the concentration dependency on macrophage activation determined by means of nitrogen monoxide production (determined spectroscopically at OD 550 nm). NO release of restimulated macrophages using different concentrations (serial dilutions) of the macrophage activator BPPcysGlyc4armPEG as adjuvant. As positive control, the NO release of macrophages in response to serial dilutions of Malp-2 and in response to 4armPEG molecules (negative control) are shown.

FIG. 5 illustrates the humoral responses following vaccination using BPPcysGlyc4armPEG and BPPcysAda, respectively, as adjuvant. Mice were immunised by intranasal (i.n.) and subcutaneous, transcutaneous (topical vaccination) (s.c.) routes with either β-galactosidase (30 μg) alone or β-galactosidase mixed with BPPcysGlyc4armPEG or BPPcysAda on days 0, 14 and 28. At day 38 post primary immunisation, serum samples were collected and the titre of 1-galactosidase-specific antibodies was determined by ELISA. As a control, a group in which animals were immunized with β-galactosidase alone was used (A). In (B) and (C) the kinetic of antigen specific serum IgG is shown for intranasal vaccination (B) and parenteral vaccination (C), respectively. (D) demonstrates that i.n. or s.c. vaccination using BPPcysAda results in an enhanced expression of antigen specific IgG. Differences were statistically significant at $p<0.05$ (*) with respect to mice receiving antigen alone. One representative out of four independent experiments is shown. SEM is indicated by vertical lines.

FIG. 6 shows the β-gal-specific secretory IgA expression in lung and vaginal lavages of i.n. immunized mice. Differences were statistically significant at $p<0.05$ (*) with respect to mice receiving antigen alone. One representative out of four independent experiments is shown. SEM is indicated by vertical lines.

FIG. 7 shows the Th-profiles in vaccinated mice after in vitro restimulation. Cytokines secreted by in vitro re-stimulated spleen cells were determined in immunized mice by CBA. Results are expressed as cytokine concentration ratios (IL-10 the most prominent detected cytokine) (B) and (D) and the stimulation index (A) and (C).

FIG. 8 provides the analysis of beta-Gal specific IgG isotypes in sera of immunized mice. Anti-beta-Gal specific IgG isotypes of the groups immunized with PBS, (control) beta-Gal+either BPPcysGlyc4armPEG or BPPcysPEG (FIG. 8A) or BPPcysAda or Ada alone (FIG. 8B), or beta-Gal alone of mice immunized by the i.n. or s.c. route were determined by ELISA. Results are expressed as end point titers. IgG titers represent the mean of five animals per experimental group. Differences were statistically significant at $p<0.05$ (*) with respect to mice receiving antigen alone. One representative out of four independent experiments is shown. SEM is indicated by vertical lines.

FIG. 9 provides the cytokine profile (IFNγ, IL-4 and IL-2) secreted by in vitro re-stimulated spleen cells from mice vaccinated with either BPPcysGlyc4armPEG or BPPcysMPEG (A), or BPPcysAda (B) and the model antigen β-gal (30 μg) alone. Results are expressed as spot forming units with subtracted background in the immunized groups with respect to the non-immunized control mice. Differences were statistically significant at $p<0.05$ (*) with respect to mice receiving antigen alone.

FIG. 10 provides specific examples of the polyalkylene units usable as part of the conjugate moiety according to the present invention.

FIG. 11 shows a particularly preferred conjugate according to the present invention, BPPcysGlyc4armPEG.

FIG. 12 demonstrates that the BPPcysGlyc4armPEG is stable after storage for 2 month at room temperature.

FIG. 13 is a scheme of the synthesis of BPPcysGlyc4armPEG.

EXAMPLES

Synthesis of BPPCysAda 0.1 mmol (~27 mg) of 3'-Amino-3'-deoxyadenosine (3'-Ada) was dissolved in 10 ml DMSO by excluding humidity. Afterwards 3'-Ada was incubated for 30 min. with 0.125 mmol BPPCysGlyc (112 mg), 0.12 mmol diisopropylcarbodiimide (DIC, 18.6 μl) and 0.12 mml 1-hydroxybenzoltriazol (HOBt, 16.2 mg). After in incubation overnight, the compound was dried by vacuum, the rest was mixed with methanol and as drop-out one remain an amorphous white solid powder (67 mg, yield 59%). 47 mg of this compound was spiked with 1 ml of 20% piperidine (in dimethylfomamide (DMF)) and dried by vacuum after 15 min. The faint was cleaned by column chromatography (SC) which was filled up with silica gel (eluent: dichlormethan and methanol in a ratio of 9:1). After these steps, 22 mg (yield 60%) of an amorphous white solid powder is obtained. The chemical structure was analyzed by $^1$H-NMR and mass spectral analysis. There are two possibilities to optimize the solubility and stability of BPPCysAda: a) selective phosphorylation of the 5'-OH group or b) pegylation of the position 6 of the adenine ring structure.

Figure 13:
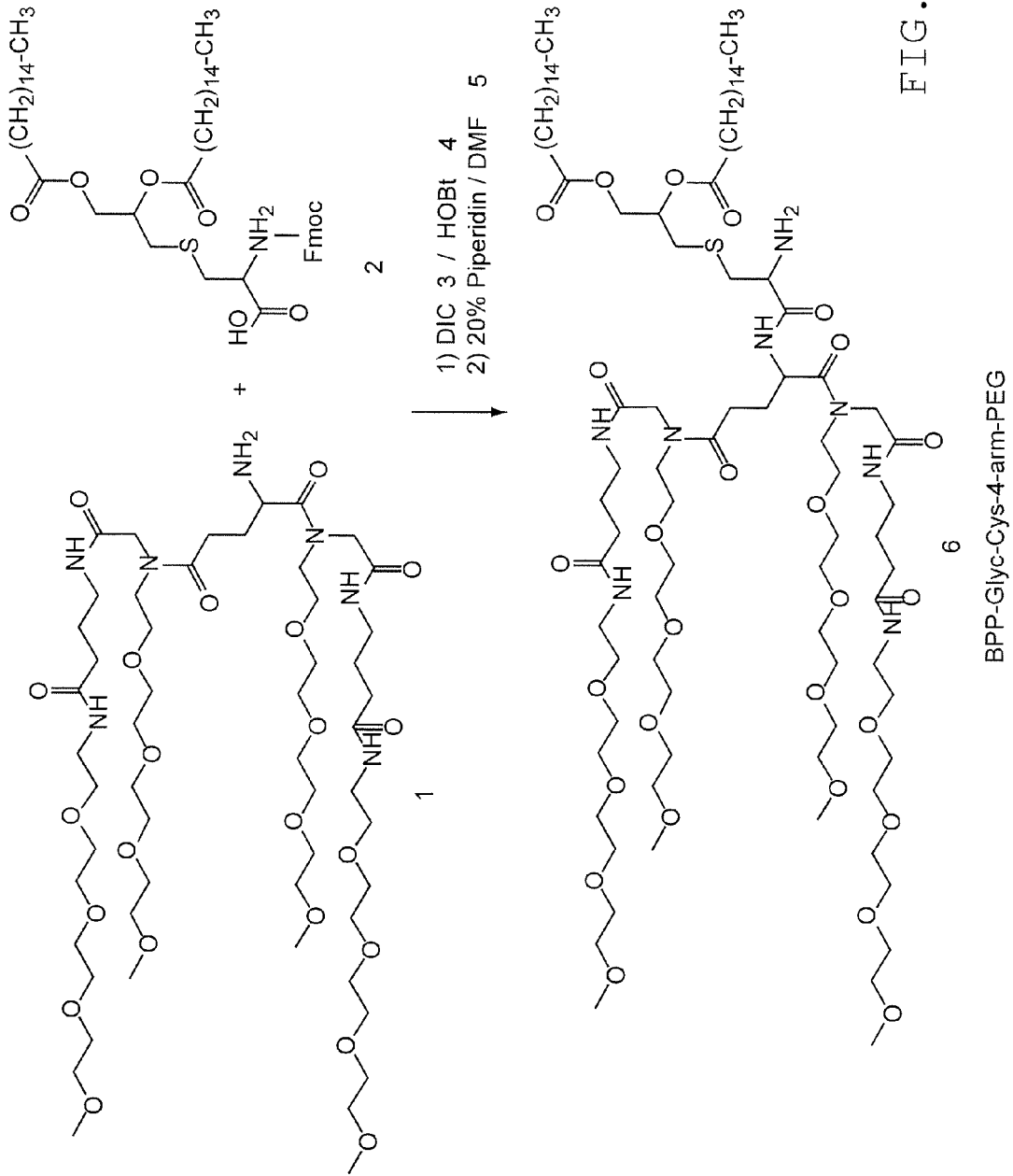
FIG. 13.

Synthesis of BPPcysGlyc4armPEG 433 mg (0.48 mmol) of compound 2 (see FIG. 13) was dissolved in 10 ml anhydrous dichlormethane (DCM). After short incubation, 80MI Diisopropylcarbodiimid (0.52 mmol) 3 and 52 mg of anhydrous Hydroxybenztriazol (0.38 mmol) 4 was added to the solution. After 15 min, the solution was completed with 216 mg of Celares 4armPEG (0.17 mmol) 1 and 2.5 ml of anhydrous dimethylformamid (DMF). After mixing the solution overnight under exclusion of humidity, the probe was concentrated via rotating evaporator. The residue was dissolved in a small amount of DCM (about 100 μl) and purified by column chromatography with silica gel and DCM/methanol in a ratio of 95:5/90:10. The fMOC-protected compound 6 was dissolved in 3 ml DMF which was completed with piperidine (20%) and after 10 min concentrated. The compound 6 was purified by column chromatography with silica gel and DCM/methanol in a ratio of 95:5 and 85:15. Subsequently, 200 mg (60% of compound 1) purified compound 6 was characterized by MS and NMR-spectral analysis.

1. In Vitro Stimulation of Primary Bone Marrow-Derived Murine Dendritic Cells with BPPcysGlyc4armPEG or BPPcysAda.

Experimental protocol: primary bone marrow-derived dendritic cell cultures were obtained from BALB/c mice following in vitro maturation of precursors in the presence of recombinant GM-CSF ($5\times10^4$ U/ml), according to established protocols. Mature dendritic cells were stimulated with 10 ng/ml of *E. coli* lypopolysaccharide (LPS) or 5 ng/ml of BPPcysGlyc4armPEG, after 12, 24 and/or 48 h stimulation cells were analyzed by flow cytometry to assess the expression of surface markers which are relevant for their antigen presentation capacity.

In order to identify compounds which may have potential as adjuvants for in vivo applications in the vaccinology field, a first in vitro screening based on the used of primary cultures of bone marrow-derived dendritic cells was established. Dendritic cells were selected since they represent the most efficient antigen presenting cells and they play a key role by primary immune responses. In fact, they are the only cell type able to activate resting T cells initiating primary immune responses in vivo. Thus, dendritic cell cultures were treated with the tested moieties or LPS, which was used as a positive control. At different time intervals, samples were taken, stained with fluorescent-labeled antibodies specific for cellular markers critical for the antigen presenting capacities of dendritic cells, and analyzed by flow cytometry.

Figure 1A:
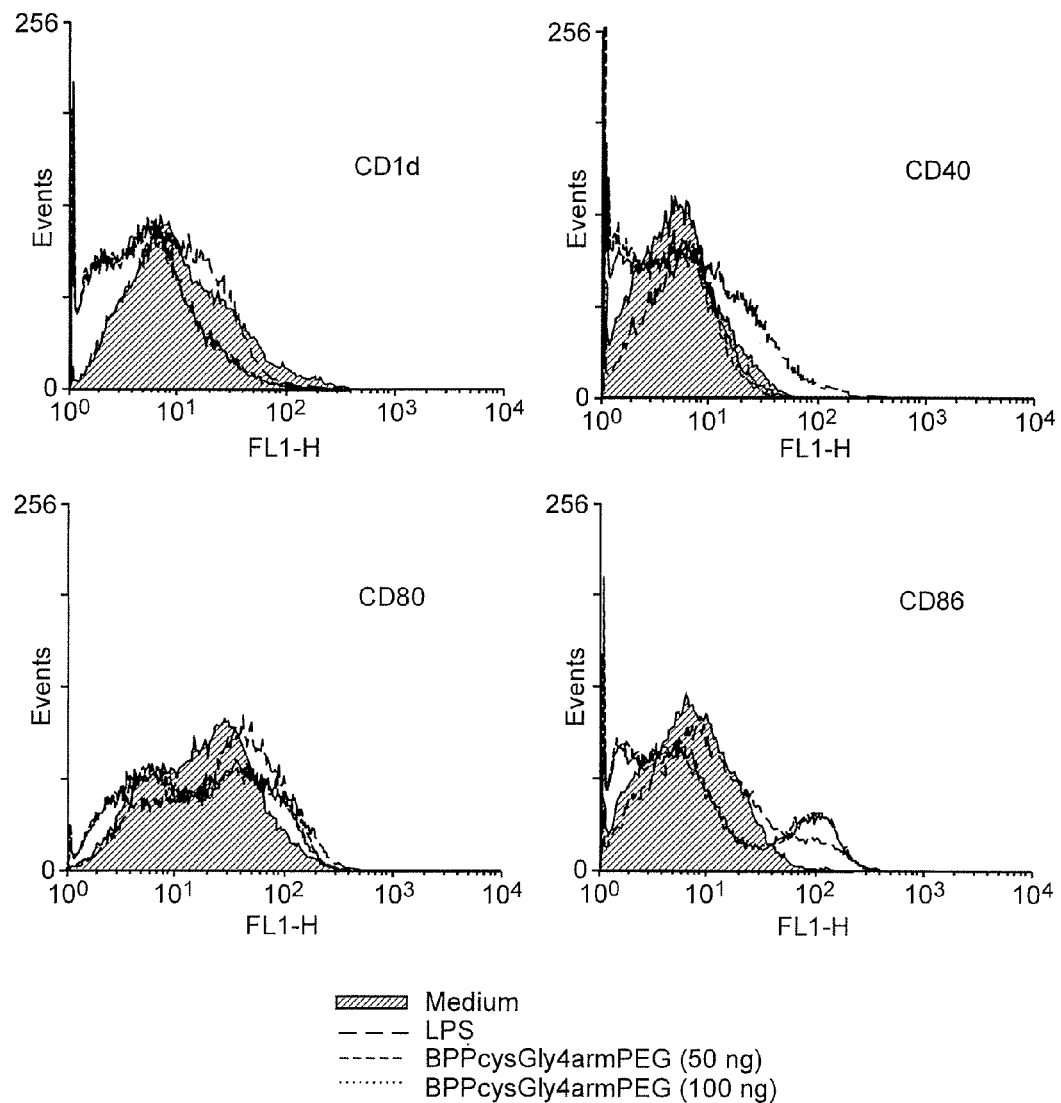
FIGS. 1A-1C show the results for In vitro studies using primary dendritic cells. Primary bone marrow-derived dendritic cell cultures were obtained from BALB/c mice by in vitro maturation of precursors using recombinant GM-CSF (5.times.10.sup.4 U/ml). Mature dendritic cells were stimulated with 10 ng/ml of *E. coli* lypopolysaccharide (LPS) or 50 and 100 ng/ml of BPPcysGlyc4armPEG and BPPcysAda, respectively. Then, cells were double-labeled with antibodies specific for CD11c (dendritic cell marker) in combination with anti-CD40, anti-CD54, anti-CD80, anti-CD86, anti-MHC class 1, or anti-MHC class 11 antibodies. The expression of CD40, CD80, CD54, CD86, anti-MHC class 1, and MHC class 11 in CD11c-gated cells were analyzed by flow cytometry.

The obtained results (FIG. 1) demonstrated that in contrast to the positive control, the expression of CD54, and the co-stimulatory molecules CD86 and CD80 were up-regulated in BPPcysGlyc4armPEG-treated dendritic cells. On the other hand, the effect on the expression of CD40 was marginal, if any at all. Co-stimulatory molecules deliver signals which, in addition to the presentation of the processed epitopes by MHC class II molecules, are essential for the efficient activation of T cells. It has been previously reported that the adjuvanticity of well-established mucosal adjuvants, such as cholera toxin, involves the selective up-regulation of the expression of co-stimulatory molecules.

Figure 1B:
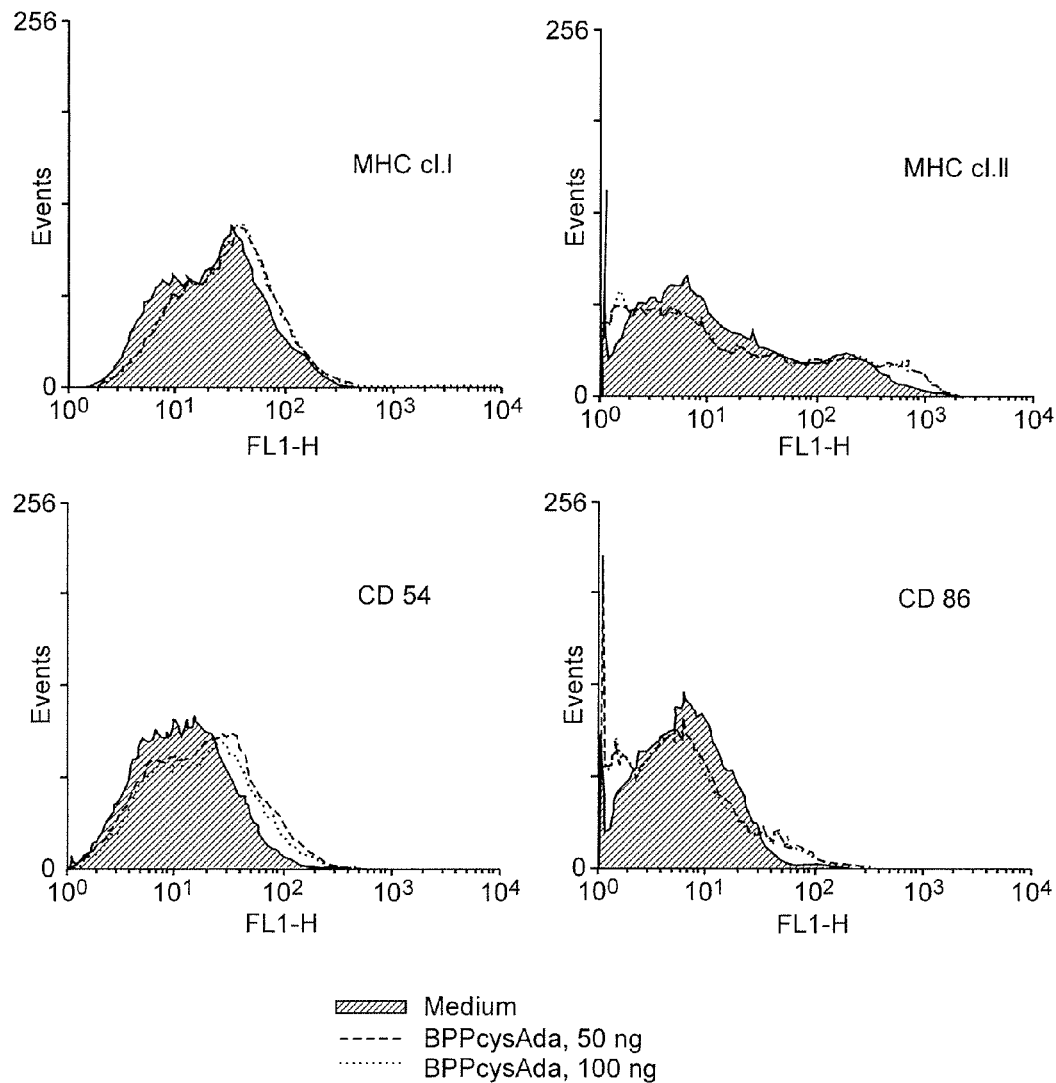
Figure 1C:
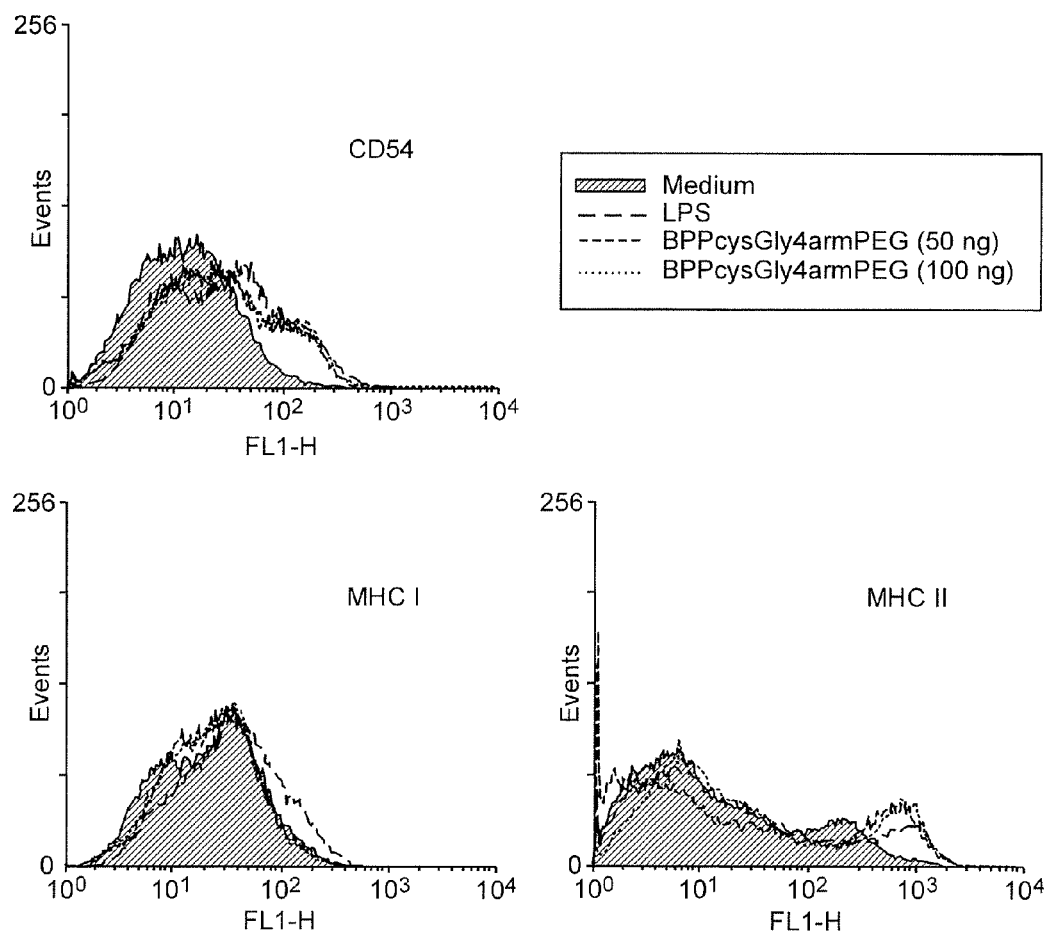

To test the stimulatory capacity of BPPCysAda on maturation and activation of bone marrow-derived DC, immature DC's were stimulated in vitro with BPPCysAda. Surface markers on CD11c+-gated DC were investigated by FACS analysis after 16 or 40 h pre-treatment. As shown in FIG. 1B the pre-incubation with 50 ng/ml of BPPCysAda resulted in an increased expression of MHC class I and II molecules. The expression of the co-stimulatory molecule CD86 was also up-regulated after stimulation with BPPCysAda. DC stimulated with BPPCysAda also showed an enhanced expression of the adhesion molecule ICAM-1 (CD54). No differences in the expression of surface markers were observed when the concentration of MALP-2 was enhanced to 100 ng/ml (not shown). The obtained results demonstrate that pre-incubation of immature DC with BPPCysAda resulted in cellular activation with increased expression of MHC class 1 and 11, CD86 and CD54.

2. BPPcysGlyc4armPEG or BPPcysAda Stimulates In Vitro Efficient T Cell-Mediated Proliferative Responses Experimental protocol: Spleens were removed and pooled for analysis of cellular immune responses. Cells were grown in RPMI 1640 supplemented with 10% fetal calf serum, 100 U/ml of penicillin, 50 µg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Lymph node and spleen cell suspensions were adjusted to $5 \times 10^6$ cells/ml in complete medium, cells were seeded with 100 µl per well in a flat-bottomed 96-well microtiter plate (Nunc) and plates were incubated for 4 days in the presence of different concentrations of soluble β-gal. Each concentration was tested in quadruplicates. During the final 18 h of culture, 1 µCi of [$^3$H] thymidine (Amersham International, Freiburg, Germany) was added to each well. Cells were then harvested on paper filters (Filtermat A; Wallac, Freiburg, Germany) by using a cell harvester (Inotech, Wohlen, Switzerland), and the amount of incorporated [$^3$H]thymidine into the DNA of proliferating cells was determined by a 1-scintillation counter (Wallac 1450, Micro-Trilux). The results are expressed as the arithmetic mean of [$^3$H]thymidine uptake in cpm.

Figure 2:
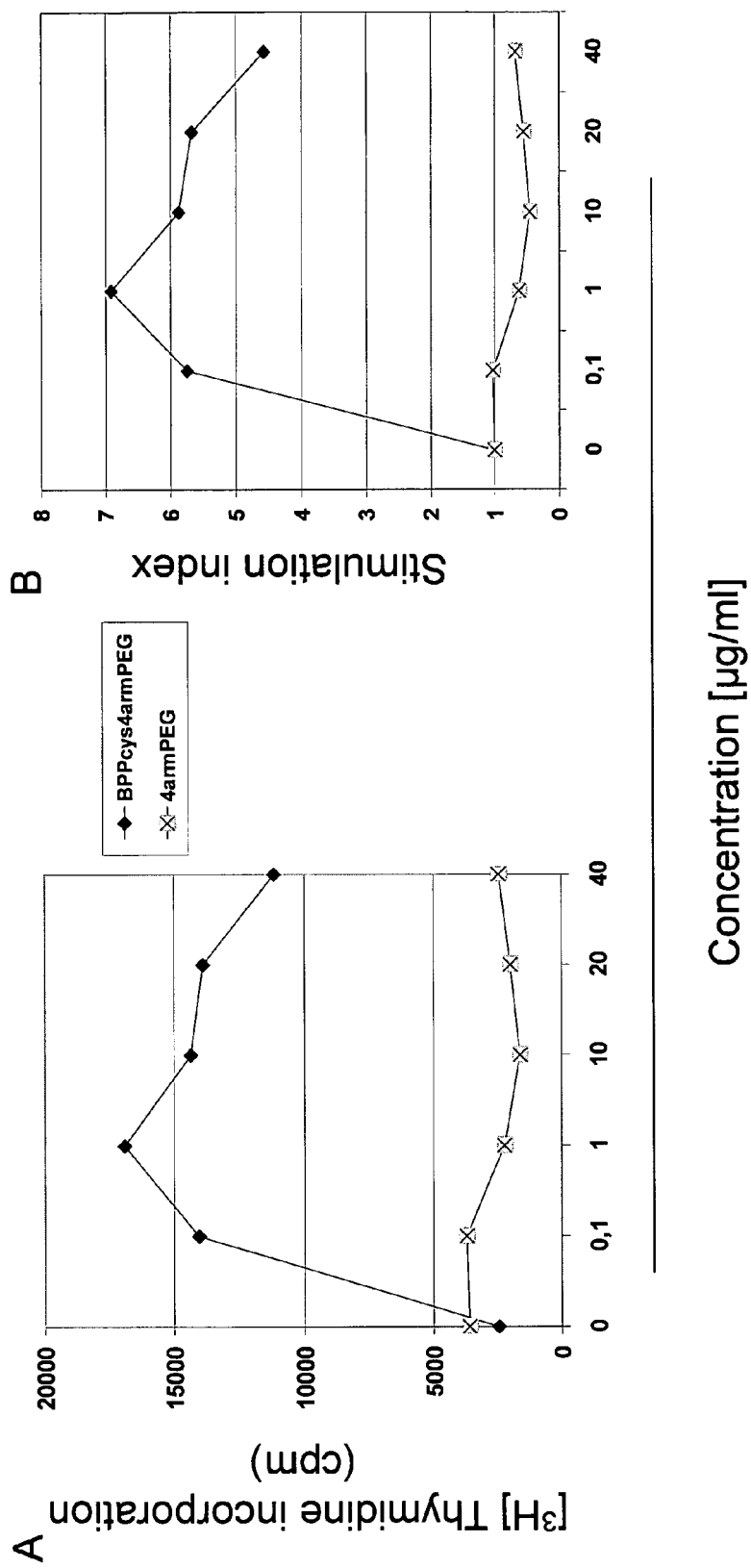
FIG. 2.
Figure 2C:
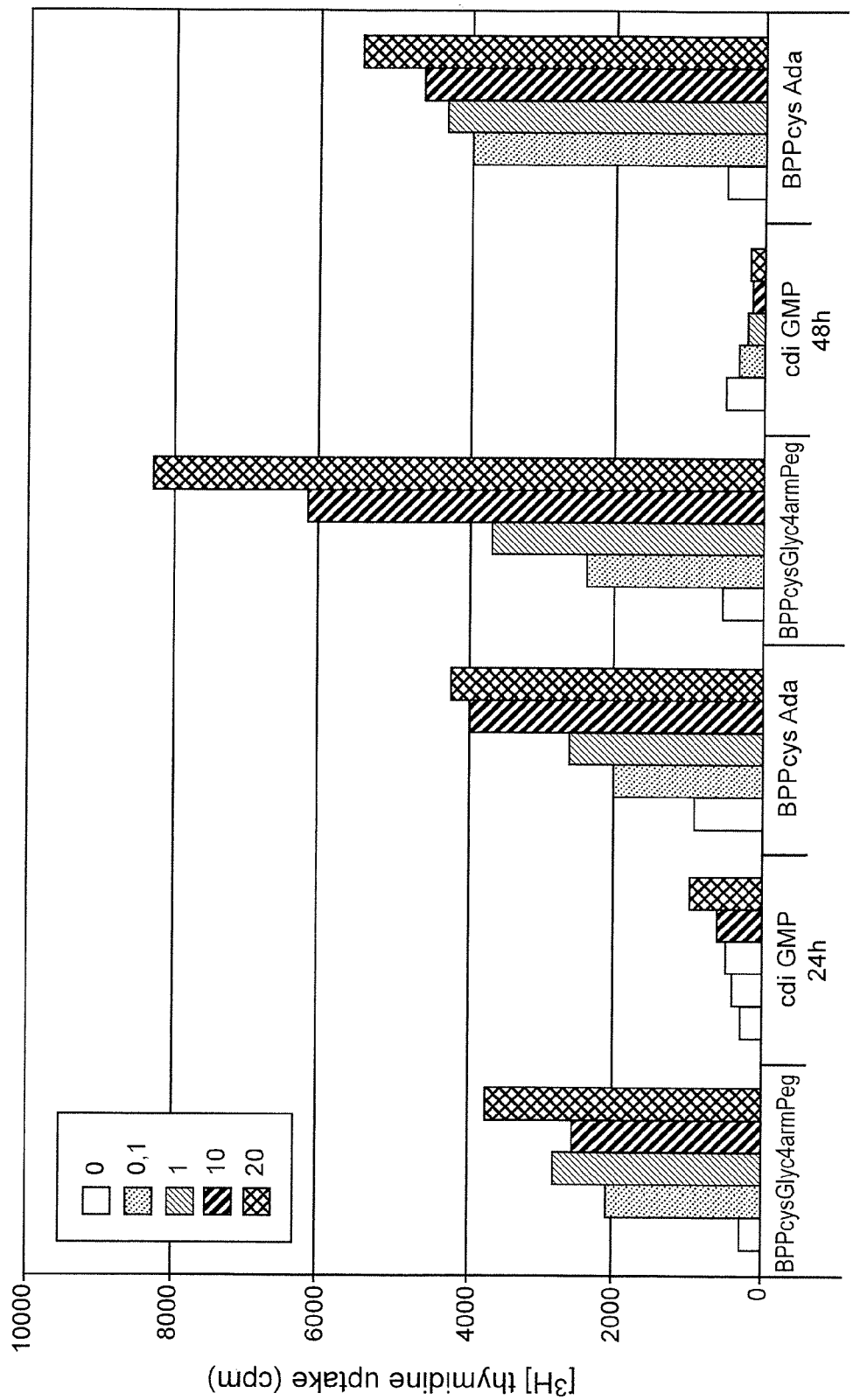

T cell-mediated immune responses were investigated 48 h by measuring the proliferation of cells recovered from spleens after restimulation with BPPcysGlyc4armPEG or BPPcysAda. 4armPEG or Ada restimulated spleen cells were chosen as a negative control. The administration of BPPcysGlyc4armPEG or BPPcysAda triggered the induction of an efficient proliferative response at systemic (spleen cells) levels with high stimulation index (FIG. 2).

3. BPPcysGlyc4armPEG or BPPcysAda Stimulates Efficient T Cell-Mediated Proliferative Responses when Co-Administered with Soluble Antigens Experimental protocol: Spleens from female BALB/c (H-2d, Harlan Winkelmann) of 6 weeks of age were removed and pooled for analysis of cellular immune responses. Cells were grown in RPMI 1640 supplemented with 10% fetal calf serum, 100 U/ml of penicillin, 50 µg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Lymph node and spleen cell suspensions were adjusted to $5 \times 10^6$ cells/ml in complete medium, cells were seeded with 100 µl per well in a flat-bottomed 96-well microtiter plate (Nunc) and plates were incubated for 4 days in the presence of different concentrations of soluble β-gal. Each concentration was tested in quadruplicates. During the final 18 h of culture, 1 µCi of [$^3$H] thymidine (Amersham International, Freiburg, Germany) was added to each well. Cells were then harvested on paper filters (Filtermat A; Wallac, Freiburg, Germany) by using a cell harvester (Inotech, Wohlen, Switzerland), and the amount of incorporated [$^3$H]thymidine into the DNA of proliferating cells was determined by a 1-scintillation counter (Wallac 1450, Micro-Trilux). The results are expressed as the arithmetic mean of [$^3$H]thymidine uptake in cpm.

Figure 3A:
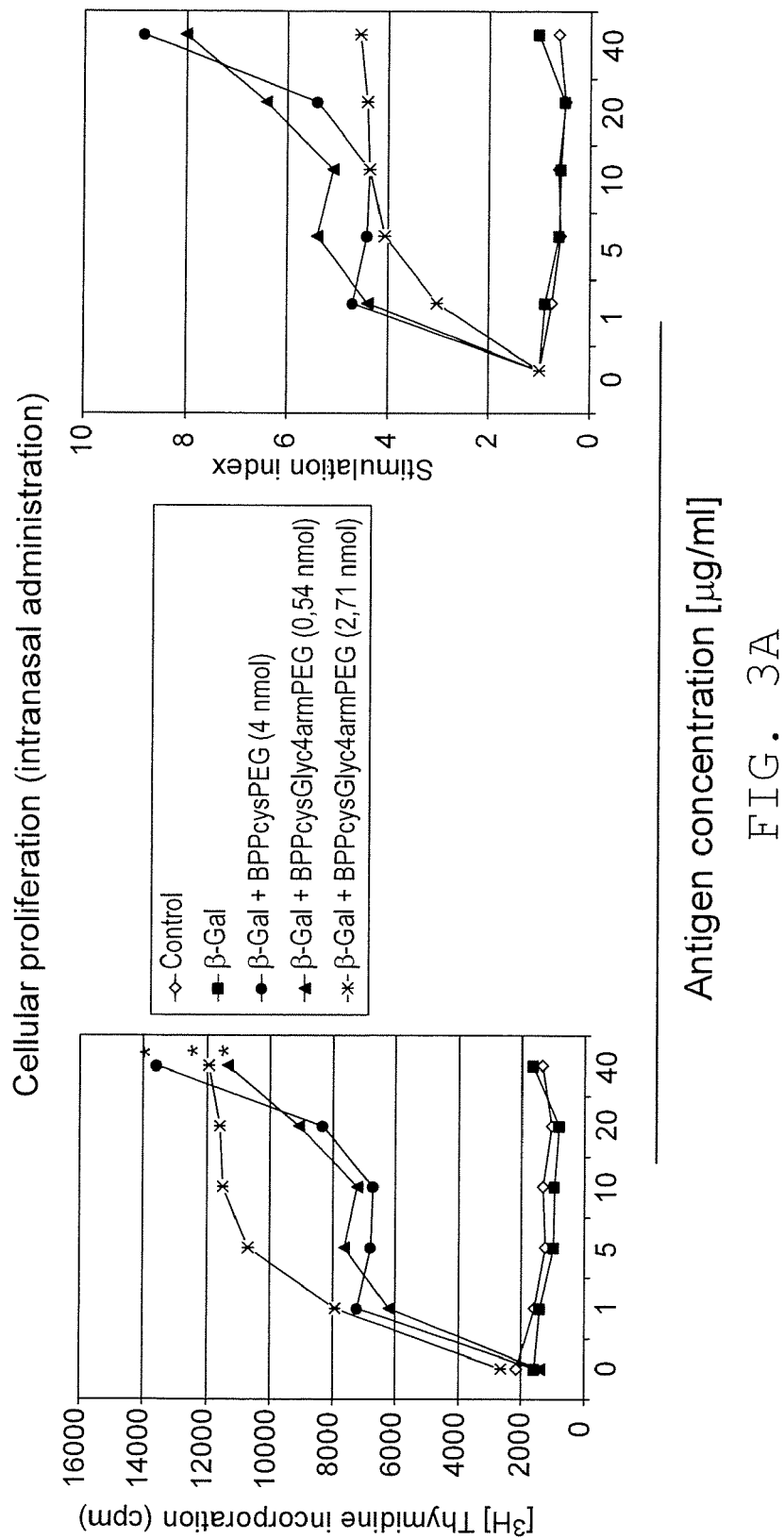
FIG. 3.
Figure 3B:
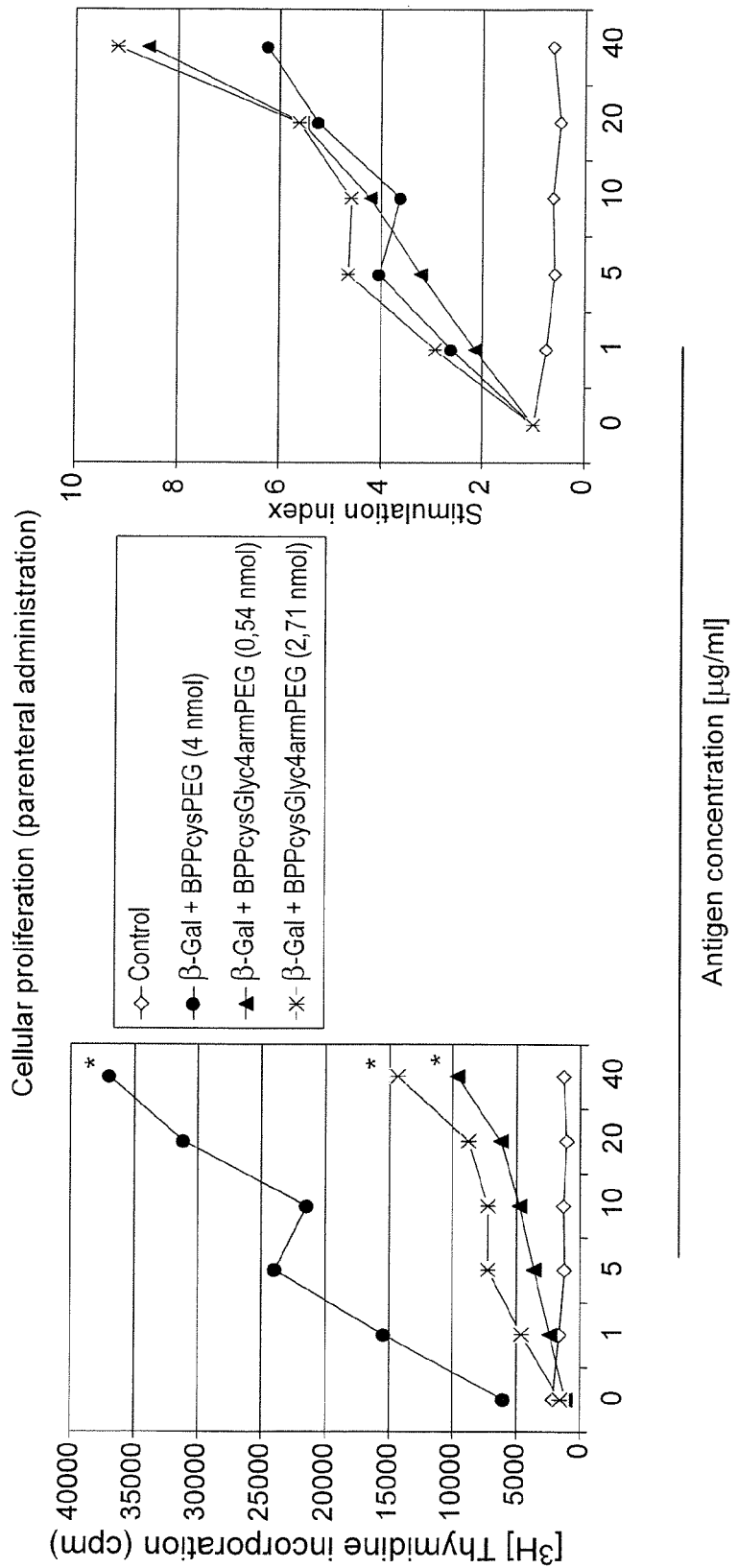
Figure 3C:
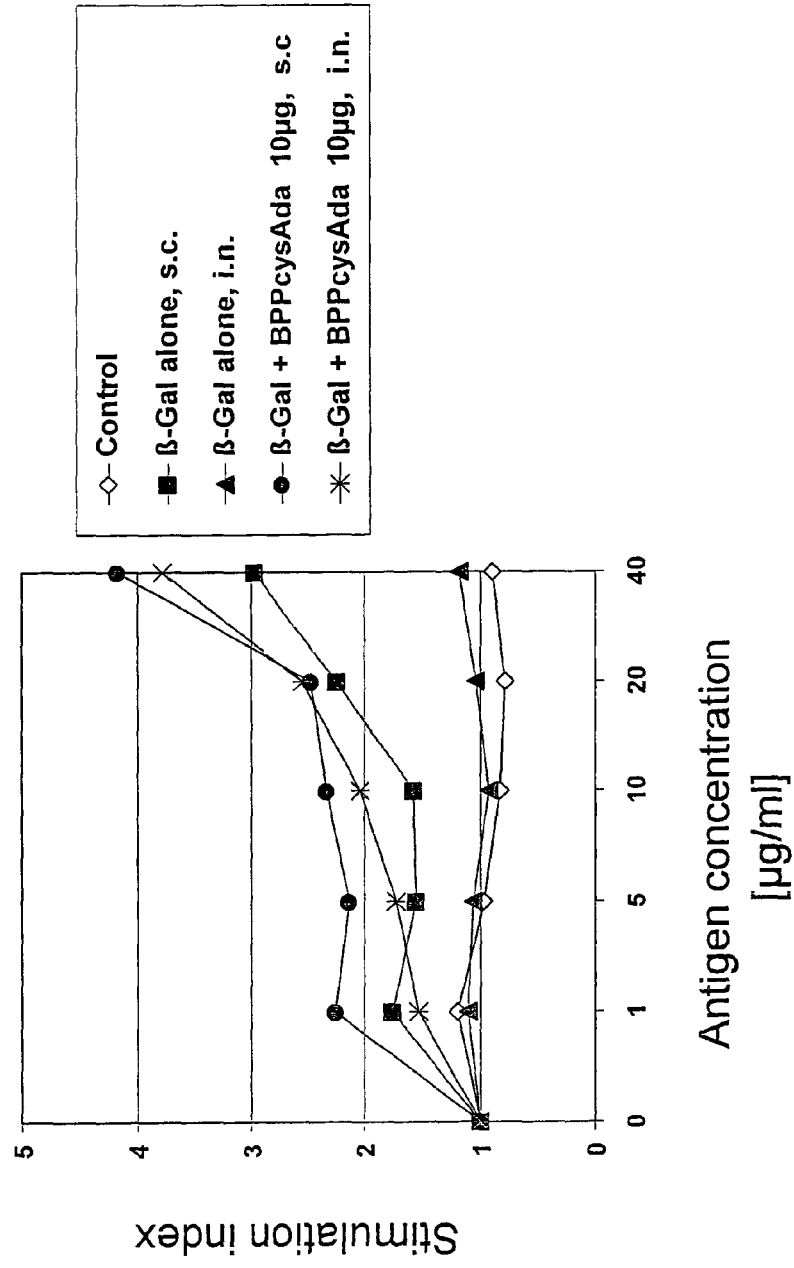

T cell-mediated immune responses were investigated at day 38 by measuring the proliferation of cells recovered from spleens after in vitro re-stimulation with β-gal. Thus, mice were immunized with either β-galactosidase alone or β-galactosidase mixed with different amounts of BPPcysGlyc4armPEG or BPPcysAda. Thirty eight days following vaccination, spleens cells were purified, re-stimulated in vitro in the presence of 20 µg/ml of β-galactosidase and their proliferative capacity was estimated by measuring the incorporation of [$^3$H]thymidine into their DNA using a 1-scintillation counter. Spleen cells from animals immunized by s.c. injection of β-gal alone, which were chosen as a positive control, exhibited a significant proliferative response as compared to the non immunized group (FIG. 3 A). A further increase in proliferation was noted in spleen cells from animals co-administrated with BPPcysGlyc4armPEG and antigen (p<0.05). Of note, the strongest T cell proliferative response was observed with spleen cells of mice immunized with BPPcysGlyc4armPEG and β-gal by the i.n. and/or s.c. route. While i.n. administration of β-gal alone failed to induce detectable cellular proliferation, co-administration of BPPcysGlyc4armPEG triggered the induction of an efficient proliferative response at systemic (spleen cells) levels, shown by the increased stimulation index (FIG. 3 B). The use of the new mucosal adjuvant BPPcysGlyc4armPEG at dosages of 0.54 nmol or 2.71 nmol, respectively, resulted in a statistically significant (p<0.05) increment of the T cell proliferation. Further, as demonstrated in FIG. 3a, BPPcysGlyc4armPEG at doses 10 fold below the doses of BPPcysPEG lead to equal levels of stimulation.

4. Nitrogen Monoxide Release Assay

In brief, peritoneal macrophages from C3H/HeJ mice were used as the macrophage source. They were cultured in 96-well microtiter plates and stimulated simultaneously with rIFN-γ and a serial dilution of macrophage activator. Insofar as necessary (i.e. R-Malp-2/standard), the macrophage activators were dissolved in 25 mM octylglucoside in the first dilution step and then diluted further with medium. After an incubating time of 45-48 hours, the nitrate was reduced with nitrate reductase and the starting substance nitrogen monoxide was determined, as the sum of nitrate and nitrite, using Griess' reagent. 1 unit (U)/ml is defined as the dilution at which half-maximal stimulation takes place.

Figure 4:
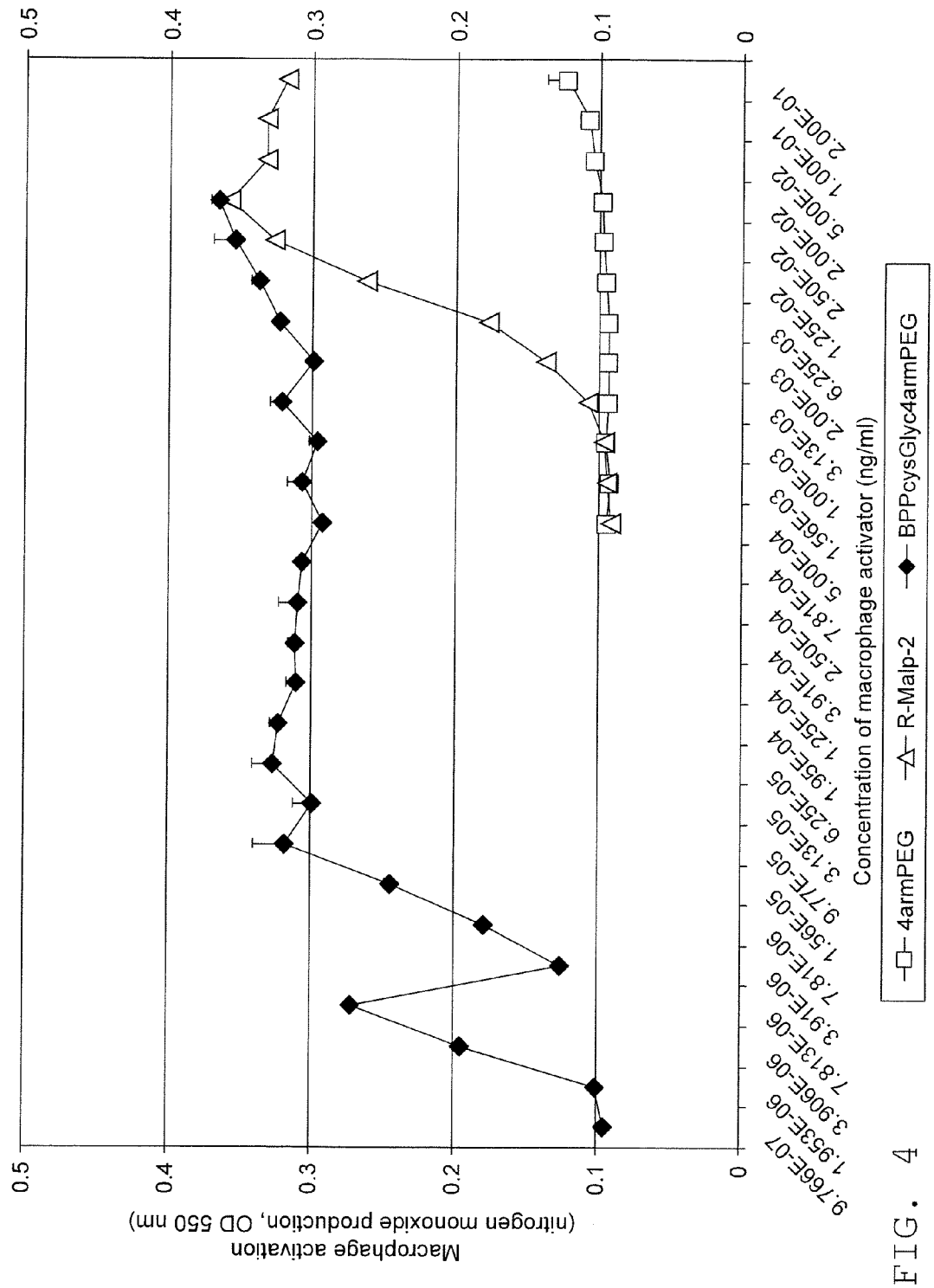
FIG. 4.
Figure 5A:
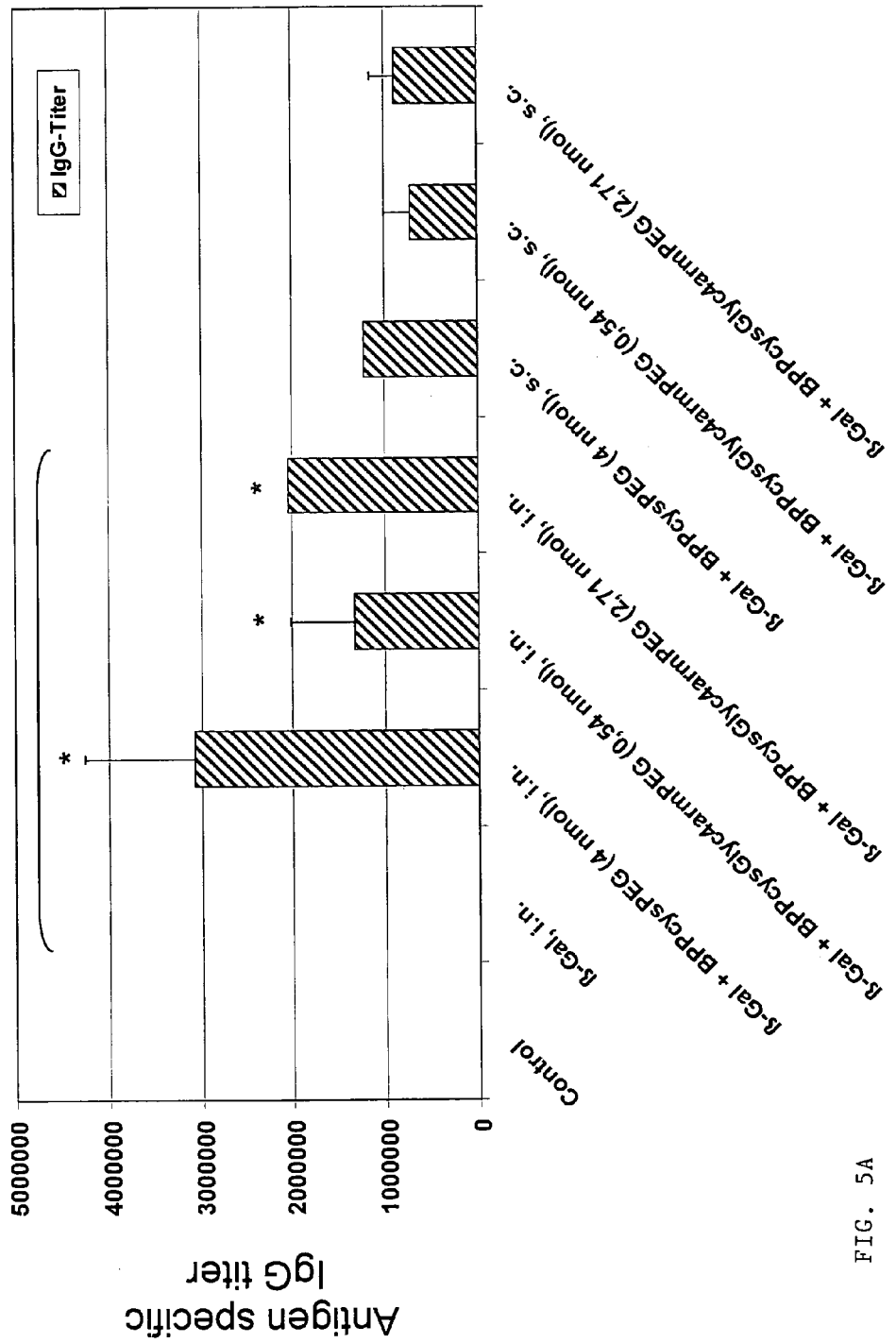
FIG. 5.
Figure 5B:
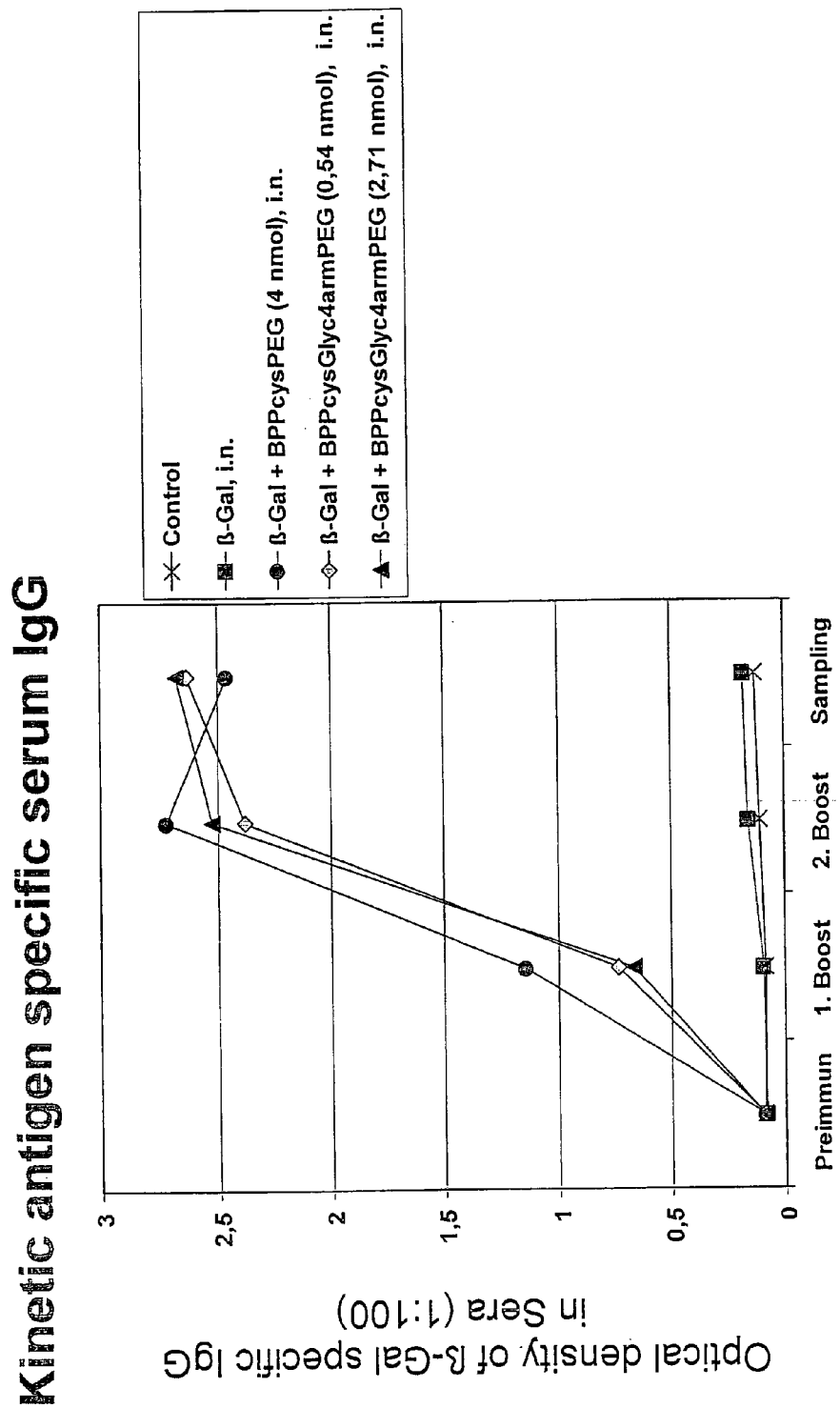
Figure 5C:
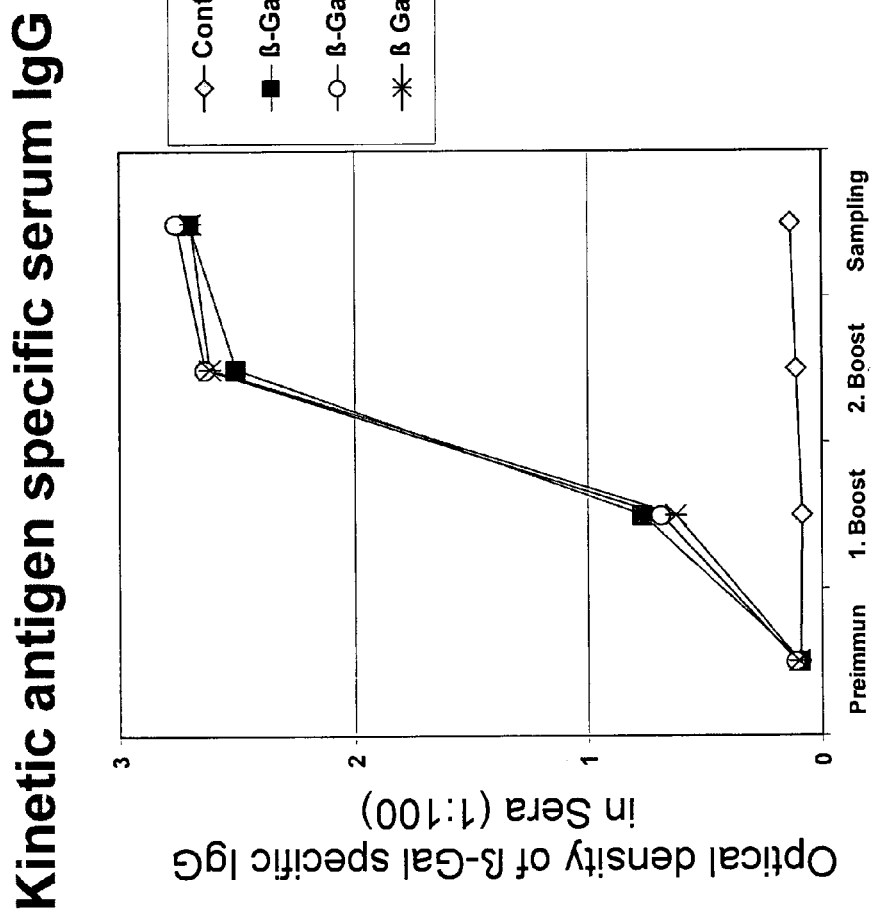
Figure 5D:
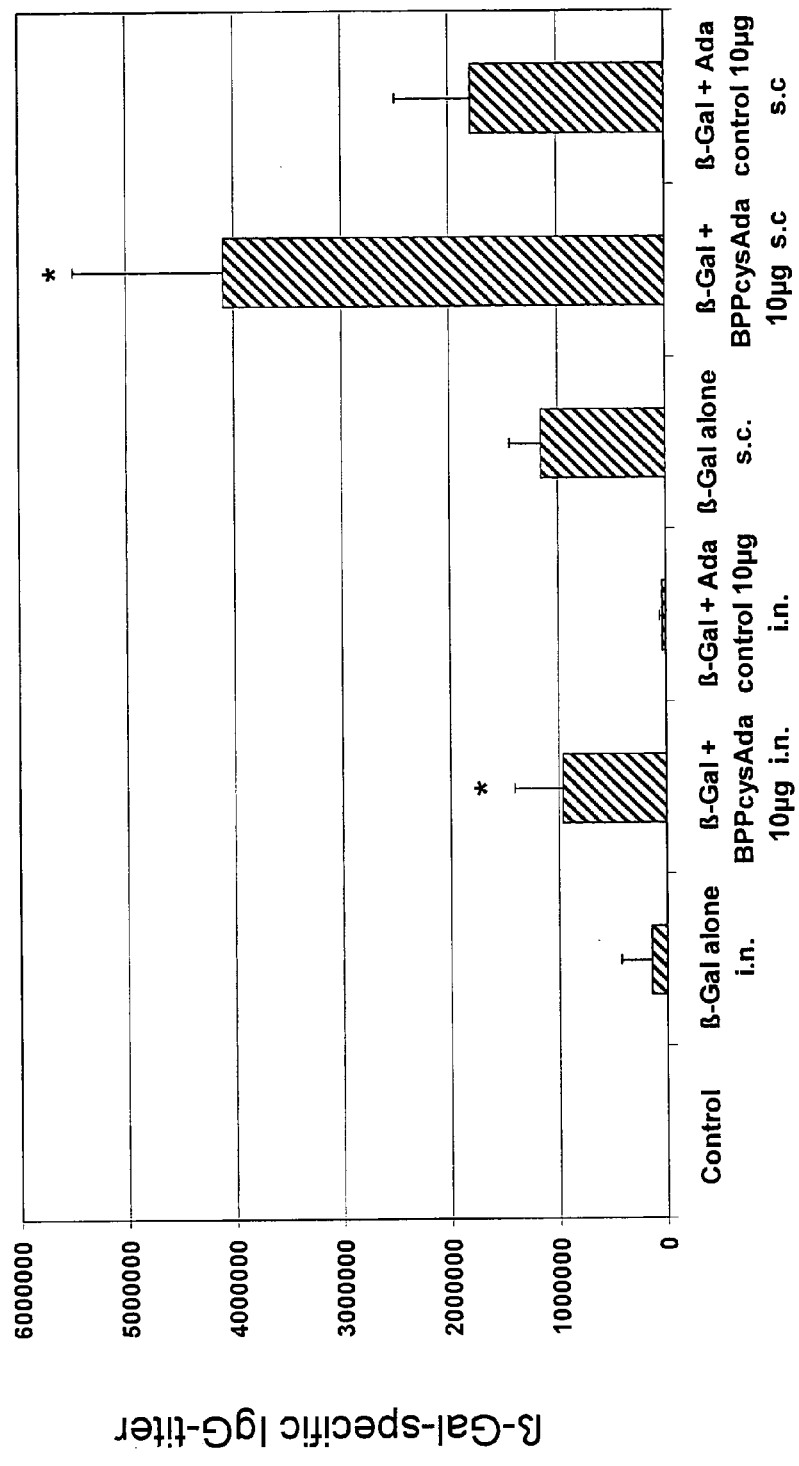

The results of the macrophage activation test are shown in FIG. 4. It can be seen from the figure that BPPcysGlyc4armPEG, i.e. a macrophage activator according to this invention, has a markedly higher potential for activating macrophages than has the known Malp-2. The FIG. 4 shows that BPPcysGlyc4armPEG already achieves the same degree of macrophage activation at a concentration which is approx. 10 to 100 times lower than that of Malp-2. The FIG. 4 furthermore shows that this outstanding and unexpected activation effect in the case of BPPcysGlyc4armPEG is not noticeably improved by adding a solubilizer, in this case octylglucoside, whereas such an addition is required for the effect of Malp-2 to be displayed optimally. The novel BPPcysGlyc4armPEG conjugate according to this invention does not, therefore, require any additional, and possibly physiologically disadvantageous, solubilization by means of an organic solvent or detergent. Another advantage of BPPcysGlyc4armPEG as compared with Malp-2 is the higher stability, which can be attributed to the fact of the 4armPEG shield.

5. Intranasal and Intraperitoneal Co-Administration of BPPcysGlyc4armPEG or BPPcysAda with a Soluble Antigen Stimulates Efficient Systemic Humoral Responses Experimental protocol: six-eight weeks-old female BALB/c (H-2d) mice were purchased from Harlan Winkelmann GmbH (Borchen, Germany) and treated in accordance with local and European Community guidelines. Groups of 5 mice each were immunized on day 1, 14 and 28 with 50 μg of β-gal (Boehringer, Mannheim, Germany), alone or with 0.54 or 2.71 nmol of synthetic BPPcysGlyc4armPEG, 4 nmol BPPcysPEG or BPPcysAda (10 μg, 10.8 nmol) or Ada alone (10 μg). For intranasal (i.n.) immunization, 10 μl were applied to each naris, whereas for the s.c. injection β-gal with or without BPPcysGlyc4armPEG was resuspended in 250 μl of PBS. Serum samples were collected at different time points (day 0, 13, 27 and 38) after immunization and stored at −20° C. prior to determination of β-gal-specific antibodies. 96-well Nunc-Immuno MaxiSorp assay plates (Nunc, Roskilde, Denmark) were coated with 100 μl of β-gal (Boehringer, Mannheim, Germany) at 5 μg/ml in 0.05 M carbonate buffer (pH 9.6) per well. Serial two-fold dilutions of sera or lavages in PBS with 1% BSA and 0.05% Tween 20 were added (100 μl/well), and plates incubated for 2 h at 37° C. After washing, biotinylated γ-chain-specific goat anti-mouse IgG (Sigma Chemie, Deisenhofen, Germany) was added, and plates were incubated for an additional 1 h at 37° C. After four washes, 100 μl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. Endpoint titers were expressed as the reciprocal $\log_2$ of the last dilution, which gave an optical density at 405 nm of 0.1 units above the values of the negative controls after 15 to 30 min of incubation.

Considering the encouraging results obtained in the preliminary studies, it was decided to analyze in detail the immune responses obtained by stimulating with BPPcysGlyc4armPEG as adjuvant by the two most effective routes, namely s.c. and i.n., and to compare it with a well-established mucosal adjuvant. Thus, the capacity of BPPcysGlyc4armPEG to stimulate efficient humoral immune responses was evaluated, by determining the serum titers of β-gal-specific antibodies in vaccinated mice. As shown in FIG. 5, i.n. administration of β-gal alone (30 μg/dose) resulted in the induction of very low antibody titers, even after the second boost. In contrast, in the presence of BPPcysGlyc4armPEG or BPPcysAda, i.n. administration of β-gal induced very high titers of specific IgG in all mice already after one dose (FIG. 5 A/B). The kinetics and the overall efficacy of the antibody responses obtained using BPPcysGlyc4armPEG were similar to those observed by administering β-gal by the s.c. route.

A significant adjuvanticity was also observed when BPPcysGlyc4armPEG or BPPcysAda was administered by the s.c. route. Specifically, co-injection of BPPcysGlyc4armPEG or BPPcysAda resulted in increased β-gal-specific IgG titers in comparison to animals immunized with β-gal alone (FIGS. 5 C and D). This difference was already present after the first immunization and was maintained upon booster injections. Similar antibody titers were detected at day 38 in animals immunized by either the i.n. or the s.c. route. However, primary responses following BPPcysGlyc4armPEG co-administration were more pronounced upon i.n. immunization.

6. Intranasal Co-Administration of BPPcysGlyc4armPEG or BPPcysAda with a Soluble Antigen Stimulates Efficient Mucosal Antibody Responses Experimental Protocol:

At day 38, mice were sacrificed and the final sampling was performed. Vaginal and lung ravages were obtained by flushing the organs with 1 ml of PBS supplemented with 50 mM EDTA, 0.1% BSA, and 10 mM PMSF. Lavages were then centrifuged to remove debris (10 min at 3000×g), and supernatant fluids were stored at −20° C. To determine the concentration of total IgA present in the lung and vaginal ravages, serial dilutions of the corresponding samples were incubated in microtiter plates that were previously coated with goat anti-mouse IgA (Sigma Chemie), as capture antibodies (100 μl/well). Serial dilutions of purified mouse IgA (Sigma Chemie) were used to generate a standard curve.

Figure 6A:
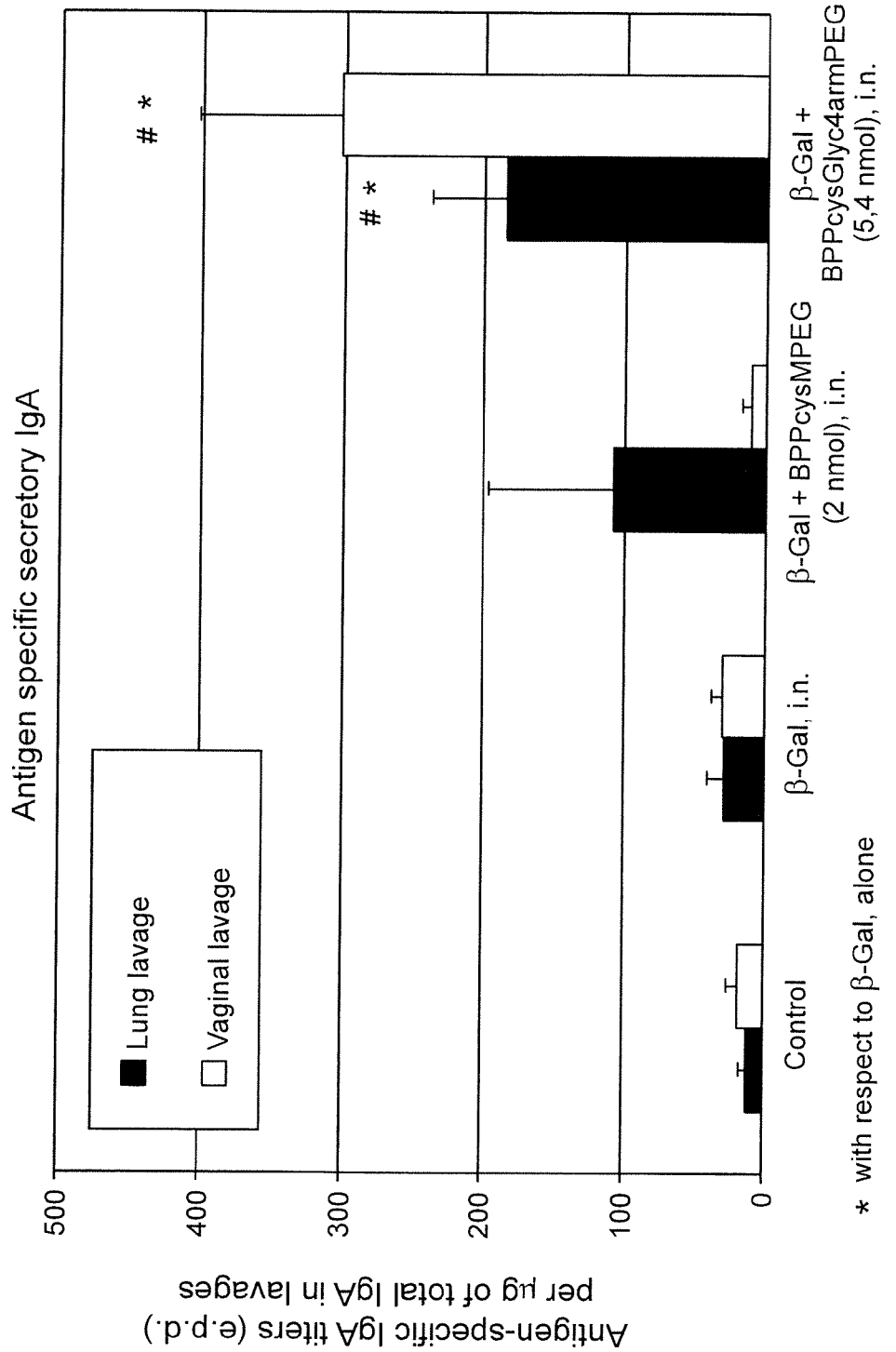
FIG. 6.
Figure 6B:
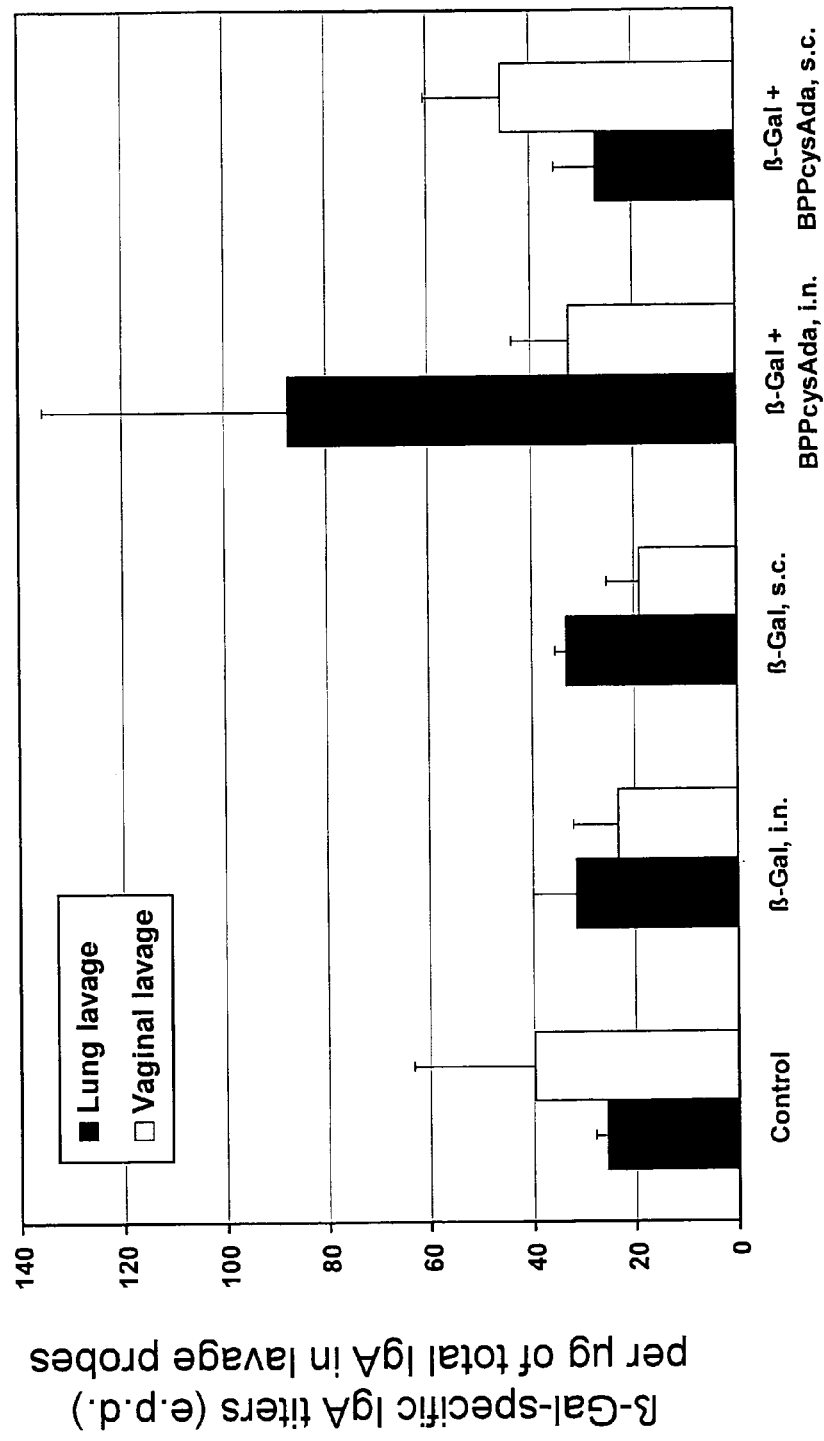

To investigate the capacity of BPPcysGlyc4armPEG or BPPcysAda to stimulate mucosal responses against antigens co-administered by the i.n. route, the production of β-gal-specific IgA in lung and vaginal ravages (FIG. 6 A) or for BPPcysAda (FIG. 6B) from immunized animals was analyzed. As control BPPcysMPEG was used. This compound comprise the conjugation of BPPcys with a PEG type which has a higher molecular weight (average molecular weight 5000 Da) instead of the commonly used PEG (average molecular weight 2000 Da). While i.n. immunization with β-gal alone failed to stimulate the production of detectable levels of β-gal-specific IgA in lung ravages, a significant increase in the levels of antigen-specific IgA was detected in animals immunized with β-gal and BPPcysGly4armPEG (FIG. 6 A). Co-administration of BPPcysGlyc4armPEG resulted in the stimulation of efficient IgA production also at distant mucosal sites, as demonstrated by the presence of significant concentrations of β-gal-specific IgA in vaginal ravages (FIG. 6 A). No statistically significant differences were observed in the levels of mucosal β-gal-specific antibodies between animals immunized with different doses of BPPcysGlyc4armPEG. The same results have been obtained using BPPcysAda (10 µg), see FIG. 6B. In BALB/c mice, intranasal administration of different doses of BPPcysAda plus β-Gal elicited significantly higher levels of β-Gal-specific IgA responses in Broncho Alveolar Lavages (BAL) and vaginal lavages (VL) as well as of β-Gal-specific IgG responses in sera than did intranasal administration with OVA alone. Additionally, intranasal administration of β-Gal with BPPcysAda significantly enhances β-Gal or OVA-specific IgG1 and IgG2a levels (not shown). Further, significantly levels of both IL-2 and IL-4 were induced in all BPPcysAda co-administered groups (FIG. 6B).

7. Analysis of the T Helper Patterns Stimulated by Using BPPcysGly4armPEG or BPPcysAda as Adjuvant Experimental Protocol:

Isotyp ELISA: 96-well Nunc-Immuno MaxiSorp assay plates (Nunc, Roskilde, Denmark) were coated with 100 µl of β-gal (Boehringer, Mannheim, Germany) at 5 µg/ml in 0.05 M carbonate buffer (pH 8.2) per well. Serial two-fold dilutions of sera or lavages in PBS with 1% BSA and 0.05% Tween 20 were added (100 µl/well), and plates incubated for 2 h at 37° C. After washing, biotin-conjugated rat anti-mouse IgG1 or IgG2a (Pharmingen, Hamburg, Germany) were added to determine IgG subclasses. Plates were incubated for an additional 1 h at 37° C. After four washes, 100 µl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. To determine the concentration of IgG subclasses in serum, standard curves were obtained by coating the wells with an isotype-specific goat anti-mouse IgG, and then by incubating with purified mouse IgG1 or IgG2a antibodies (Dianova, Hamburg, Germany).

Figure 8A:
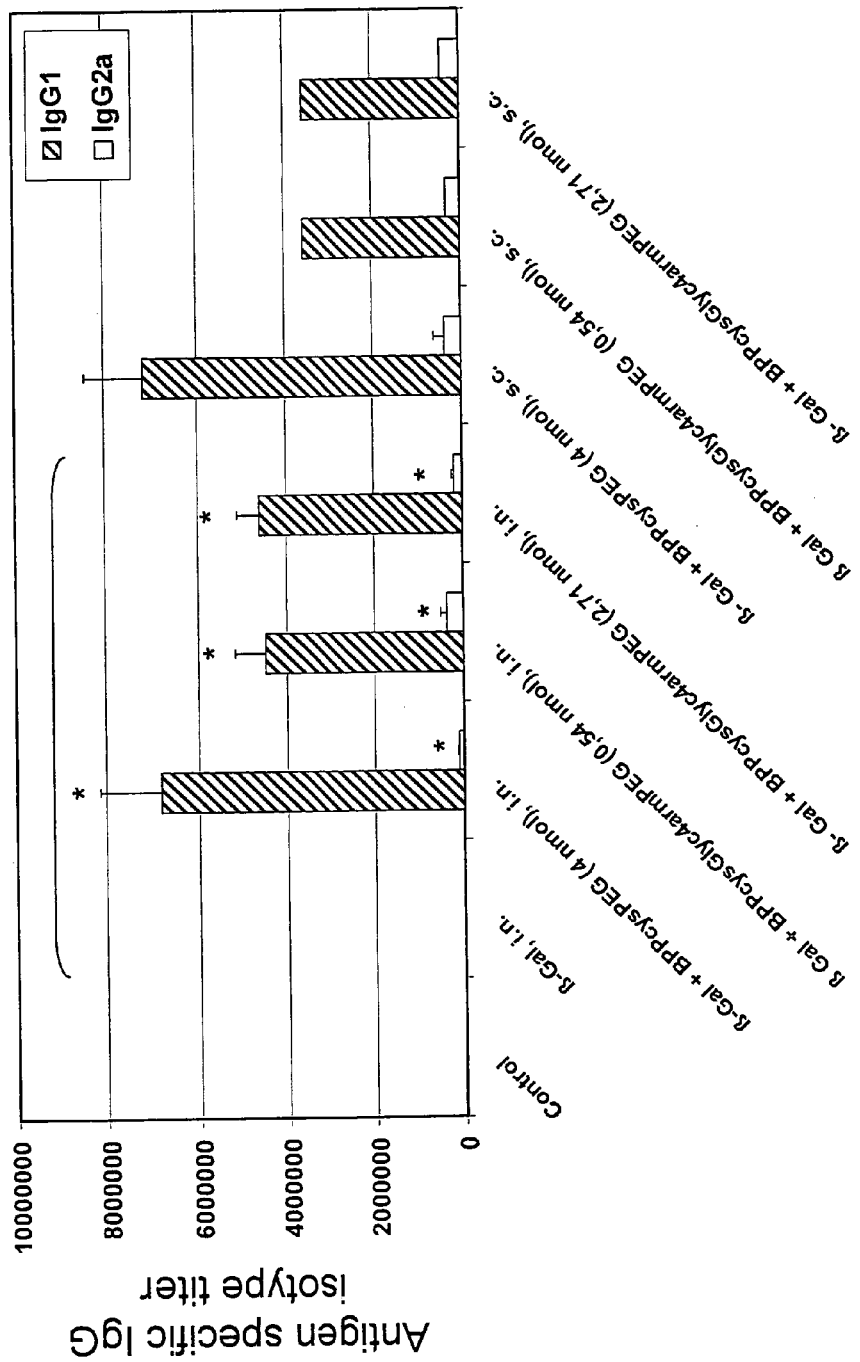
FIG. 8.
Figure 8B:
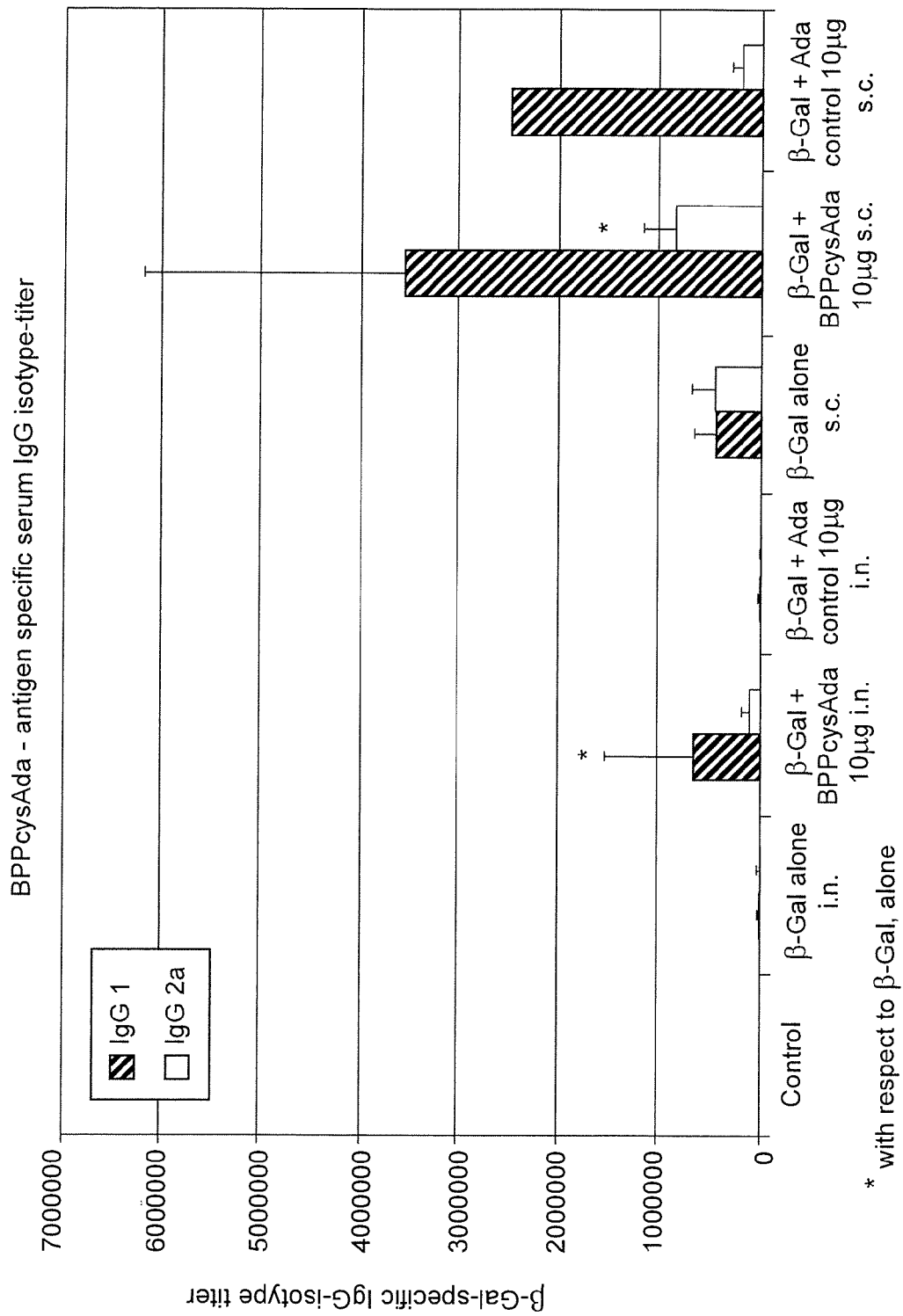

The pattern of the different subclasses of the β-gal antigen-specific IgG isotypes present in the sera of vaccinated mice is shown in FIG. 8. FIG. 8A shows the results for intranasal administration of β-Gal alone, β-Gal and either BPPcysMPEG or BPPcayGlyc4armPEG. The protocol for vaccination was identical to the protocol described in Example 2. As can be ascertained from FIG. 8, the amount of antigen specific antibodies of the IgG1subtype and the IgG2a isotype were strongly increased after intranasal administration of the antigen using BPPcysGlyc4armPEG or BPPcysAda as mucosal adjuvant. Further, also in case of systemic administration, here subcutaneous administration, the expression of the IgG1 isotype as well as of the IgG2a isotype are strongly increased for BPPcysAda, see FIG. 8B. The data represents the average titer of a group of 5 animals.

Thus, the use of c-diAMP allows eliciting a strong antigen-specific antibody response. The triggering can be seen not only after intranasal administration but also after parenteral administration.

Cytometric Bead Array: Culture supernatants from proliferating cells were collected on days 2 and 4, and stored at −70° C. Determinations of IFN-γ, TNFα, IL-2, IL-4, IL-5, IL-6, IL-10 and IL-12 were performed by cytometric bead array analysis using the commercial kit from BD, according to the manufacturer's instructions. A standard curve was generated for each cytokine by using the corresponding recombinant murine cytokines (Pharmingen). Probes were incubated at room temperature for additional 2 h. The probes were then analyzed by flow cytometry as described by the protocol of BD.

Figure 7:
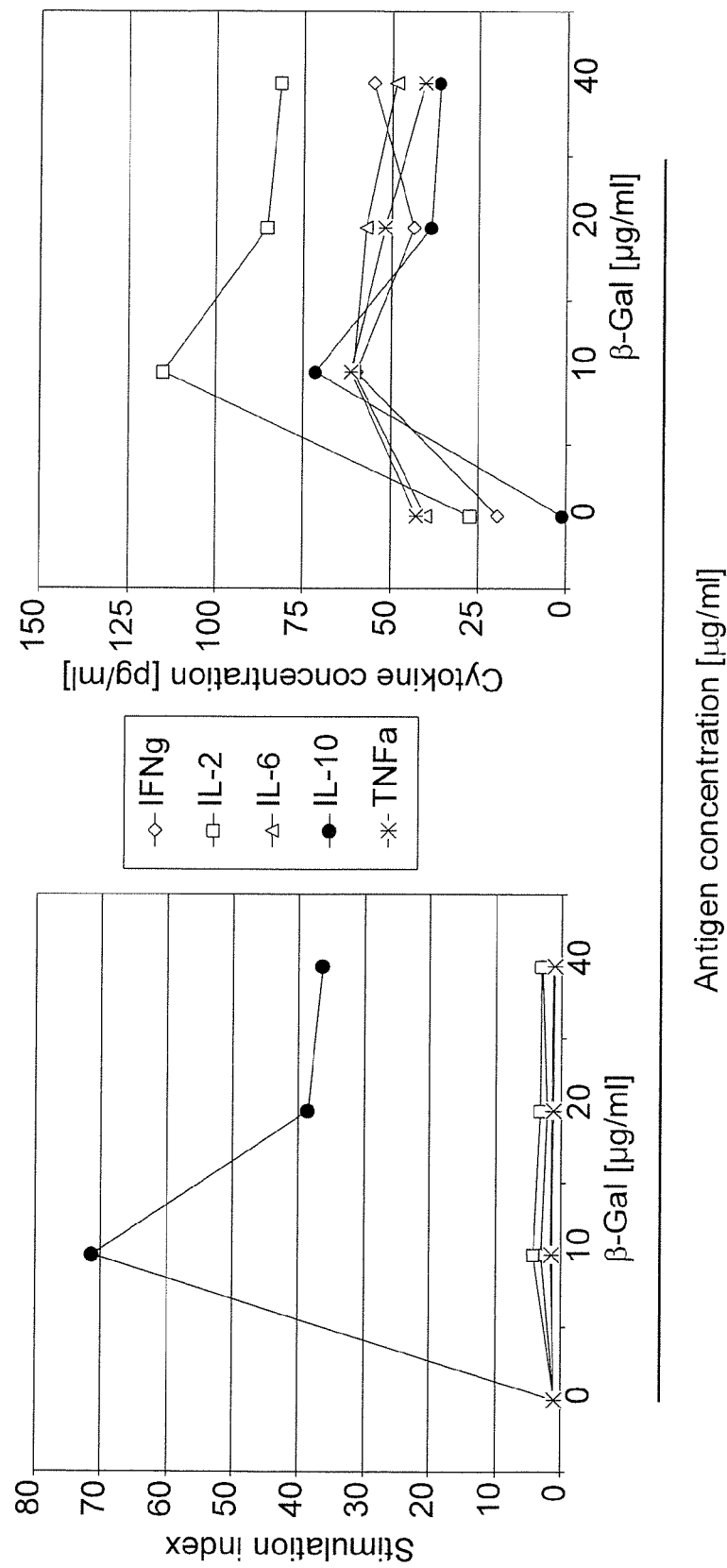
FIG. 7.
Figure 7C:
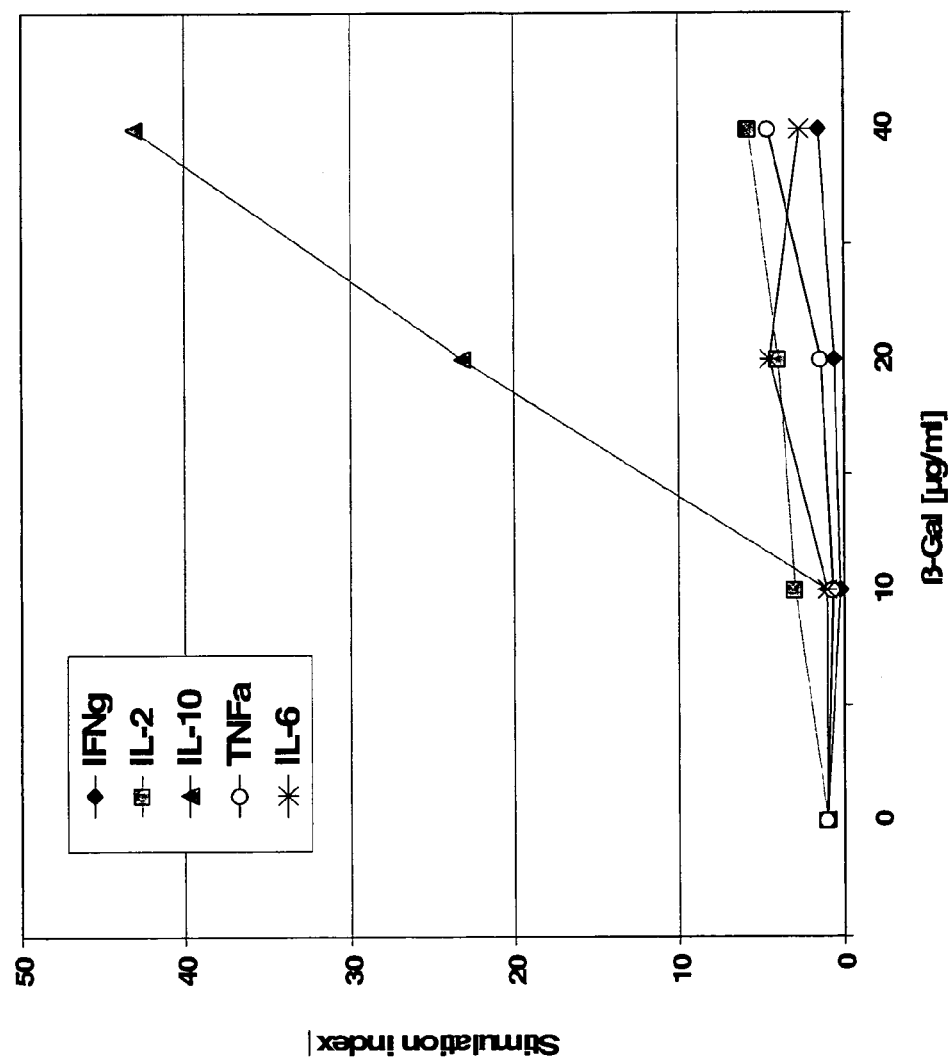
Figure 7D:
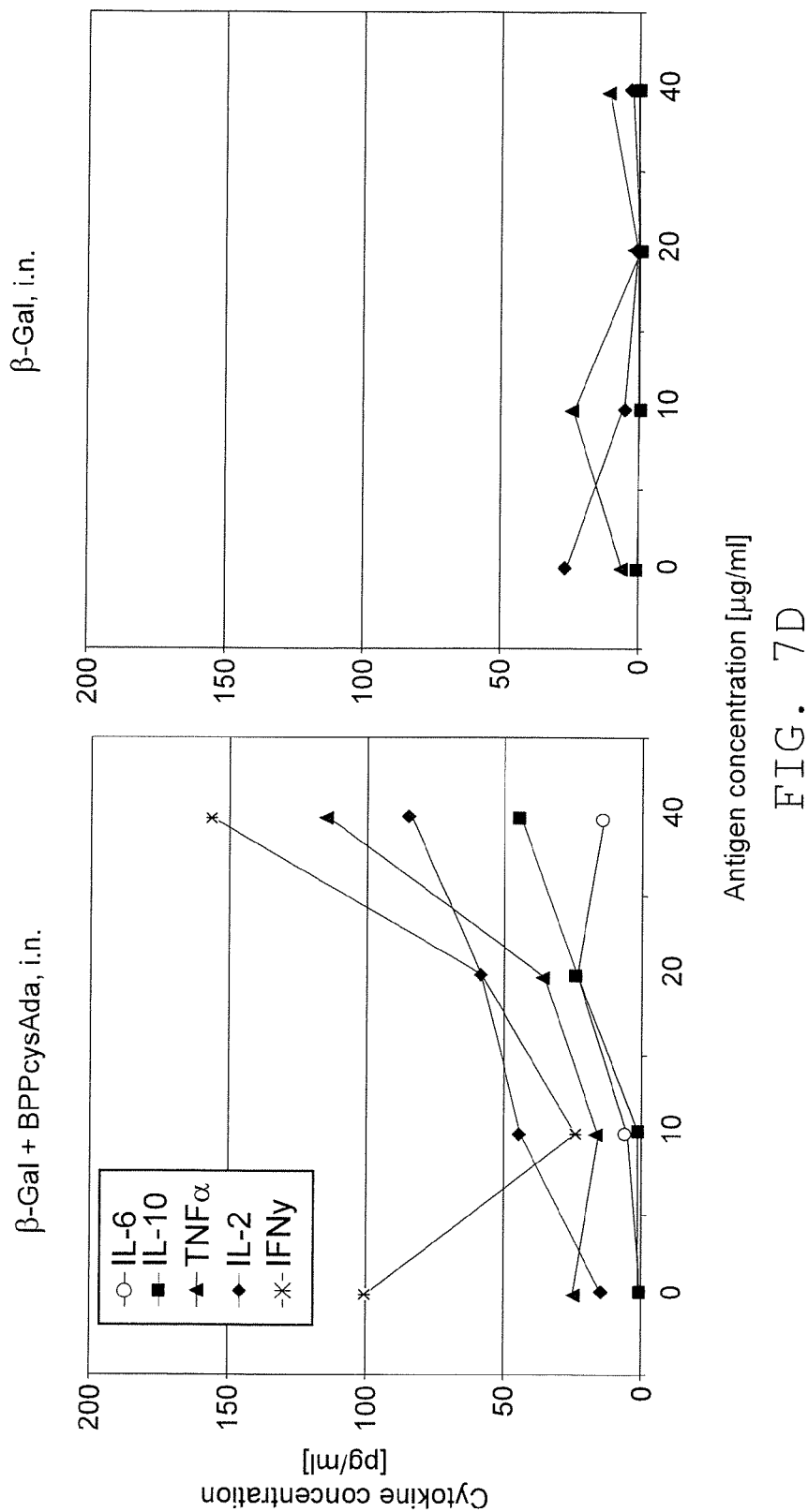

To characterize the type of Th response stimulated following immunization, the content of IFN-γ, IL-2, IL-4, IL-5, IL-6, IL-10, IL-12 and TNFα was measured in supernatants from in vitro re-stimulated spleen cells (FIG. 7). Among these cytokines, IL-10 was found to be the most prominent, suggesting that a dominant Th2 response pattern was stimulated. The levels of IL-10 were significant higher in mice vaccinated with BPPcysGlyc4armPEG by i.n. route. In fact, the strong stimulation of IL-10 secretion is congruent with the role played by this cytokine in the inhibition of cytokine synthesis by Th1 cells, the enhancement of B cells proliferation and the stimulation of IgA production.

For BPPcysAda, IL-10 production was significantly increased in spleen. A very high level of IL-10 was induced by increasing the dose of the β-Gal antigen, whereas the levels of IFNγ, TNFα, IL-2 and IL-6 showed only a weaker increase in cytokine secretion in response to the β-Gal antigen in spleen.

To assess the epitope-specific cellular immune response induced by the co-administration of BPPCysAda via intranasal, subcutaneous or intramuscular route, IFNγ-producing CD8+ T cells were analyzed after stimulating splenocytes with the MHC cl. I restricted β-Gal (TPHPARIGL) or OVA (SINFEKL) peptides. The number of IFNγ-secreting CD8+ T cells was significantly decreased in comparison to groups immunized with β-Gal or OVA alone-treated groups (not shown). These results demonstrated that mucosal and parenteral co-administration of BPPcysAda induces a Th2 dominated immune response.

Interestingly, although minor secretion of Th1-cytokines IL-2 and IFN-γ was also stimulated in cells from mice vaccinated with β-gal and BPPcysGlyc4armPEG or BPPcysAda by the i.n. route. These results confirm that, although Th2 type responses are prevalent, BPPcysGlyc4armPEG or BPPcysAda also helps the stimulate Th1 cells.

8. Analysis of the T Helper Patterns Stimulated by Using BPPcysGlyc4armPEG or BPPcysAda as Adjuvant by Elispot Experimental protocol: Spleens were removed and pooled for analysis of cellular immune responses. Cells were grown in RPMI 1640 supplemented with 10% fetal calf serum, 100 U/ml of penicillin, 50 µg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Lymph node and spleen cell suspensions were adjusted to $5 \times 10^6$ cells/ml in complete medium, cells were seeded with 100 µl per well in a flat-bottomed 96-well microtiter plate (Nunc) and plates were incubated for 4 days in the presence of different concentrations of soluble β-gal. Coat ELISPOT plate with 100 µl/well of purified capture antibody at 10 µg/ml in coating buffer, incubate at 4° C. overnight. After 6× washing steps, the plates were blocked with 200 µl/well of complete RPMI-1640 at room temperature for 1 hour. The activated cells were seeded at 100 µl per well and incubate at 37° C., in a 5% $CO_2$ humidified incubator for 24 hours or 48 hours. After 5× washing steps with washing buffer and 1× step with distilled water, 100 µl/well of the biotinylated detection antibody with a concentration of 1 µg/ml in Assay Diluent was added and incubated at room temperature for 2 hrs. After further washing steps 100 µl/well of the AV-HRP at 1/1000 dilution in Assay Diluent was added and incubated at room temperature for 30 minutes. After further washing steps 100 µl/well of AEC Substrate Solution was added and developed at room temperature for 20-60 minutes until visible spots appeared. After washing steps with (3×) with 200 µl/well distilled water, the plates were air-dried and analyzed by counting the spots by an ELISPOT reader. Each concentration was tested in triplicates.

Figure 9A:
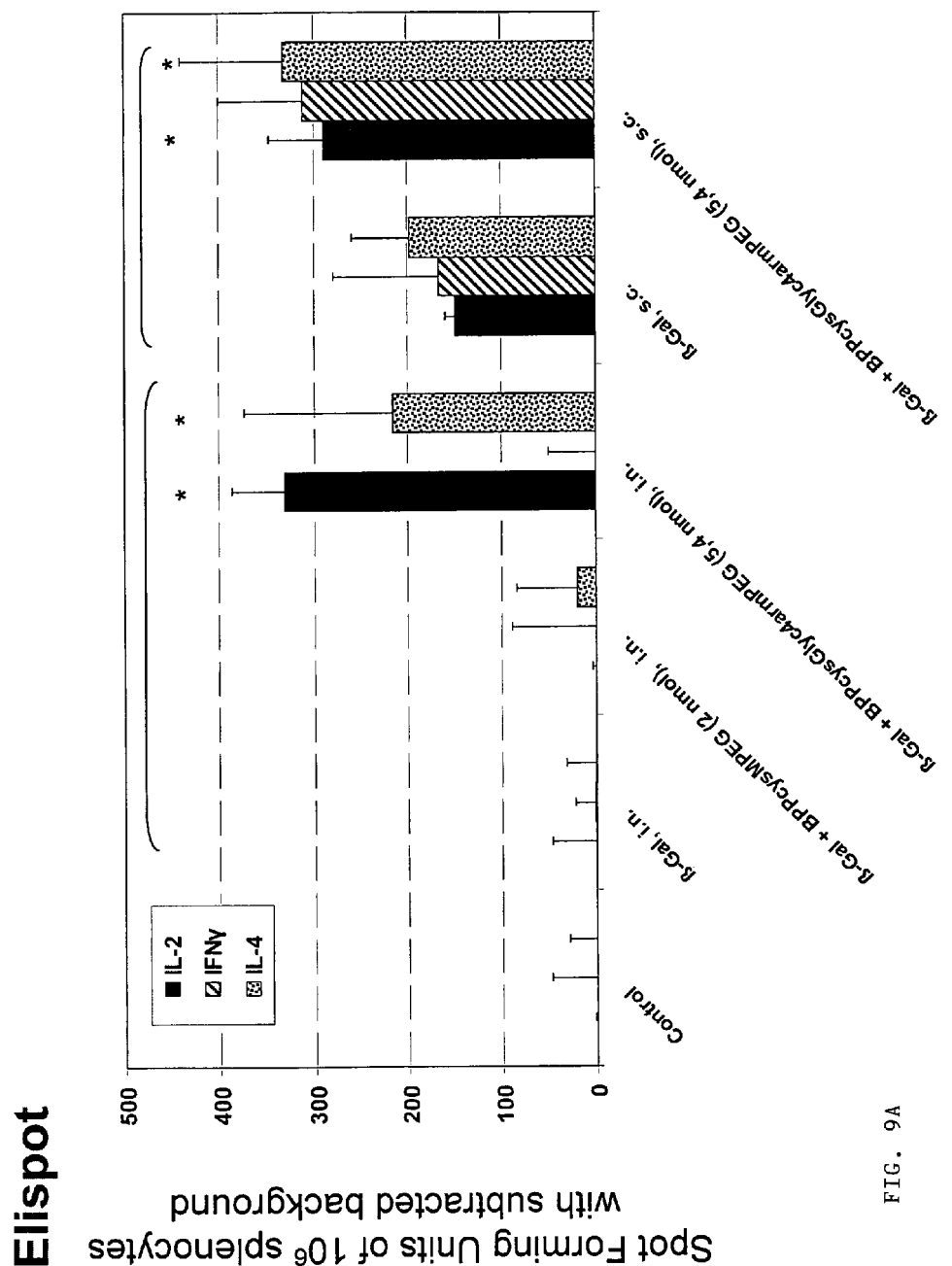
FIG. 9.
Figure 9B:
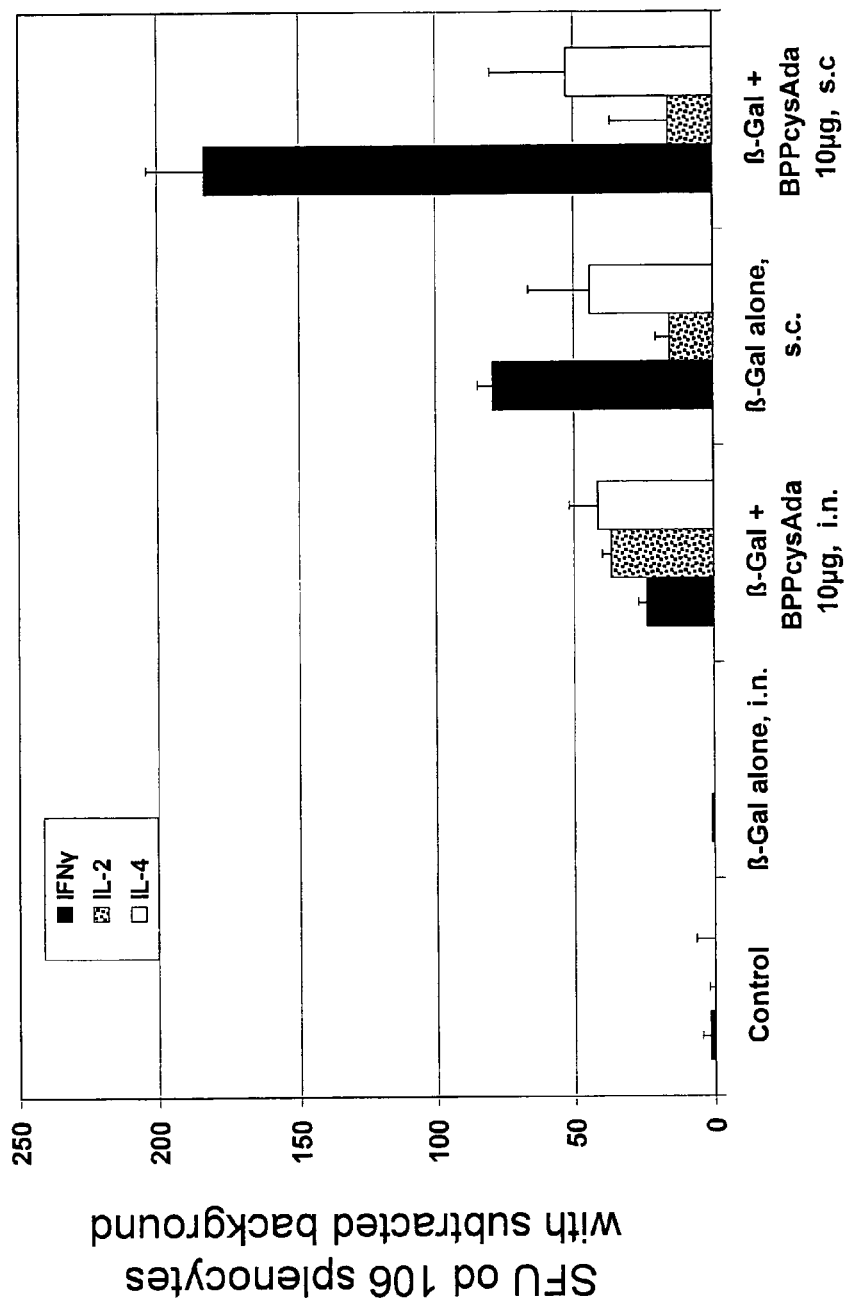
Figure 10:
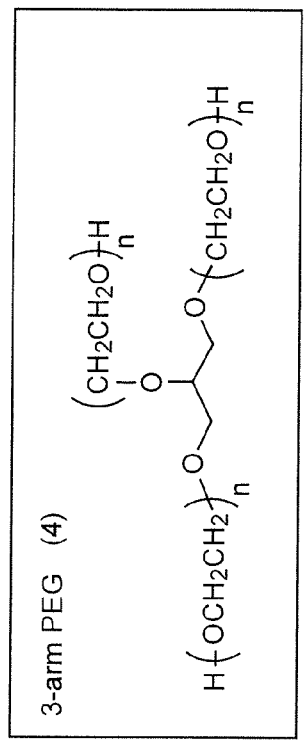
FIG. 10.
Figure 10:
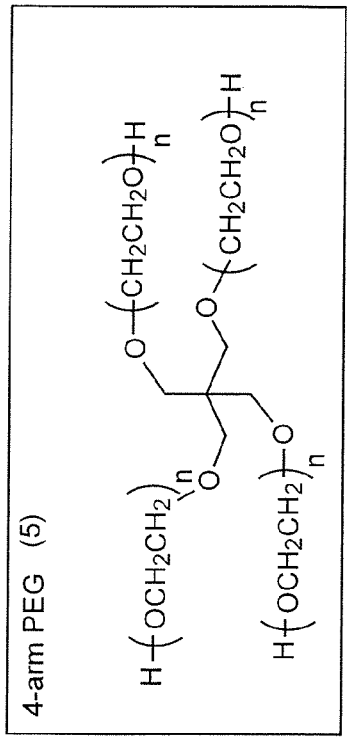
Figure 10:
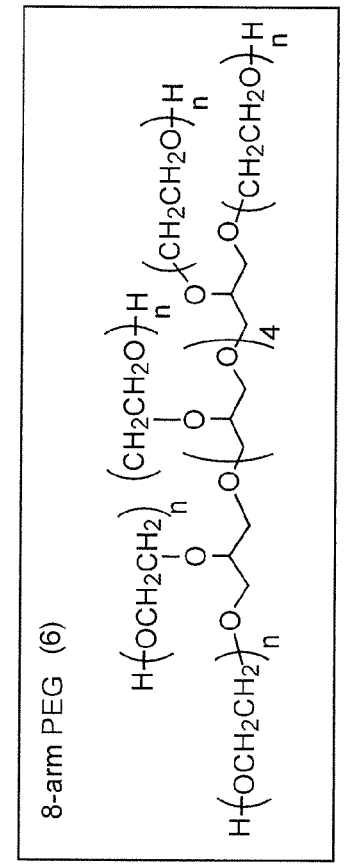
Figure 10:
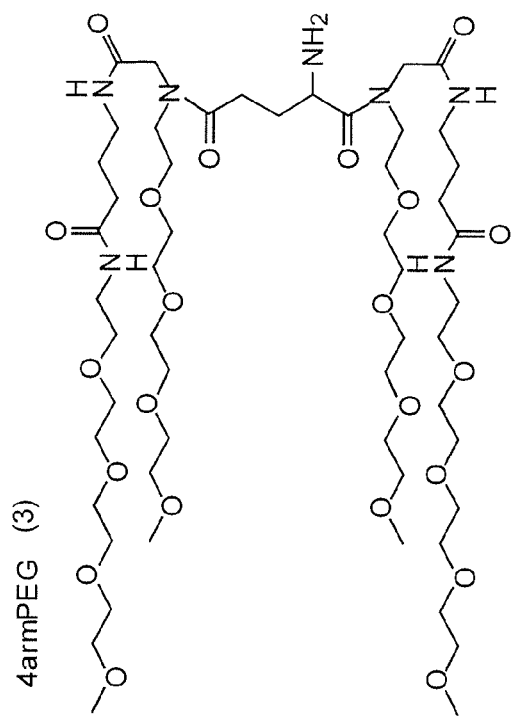
Figure 11:
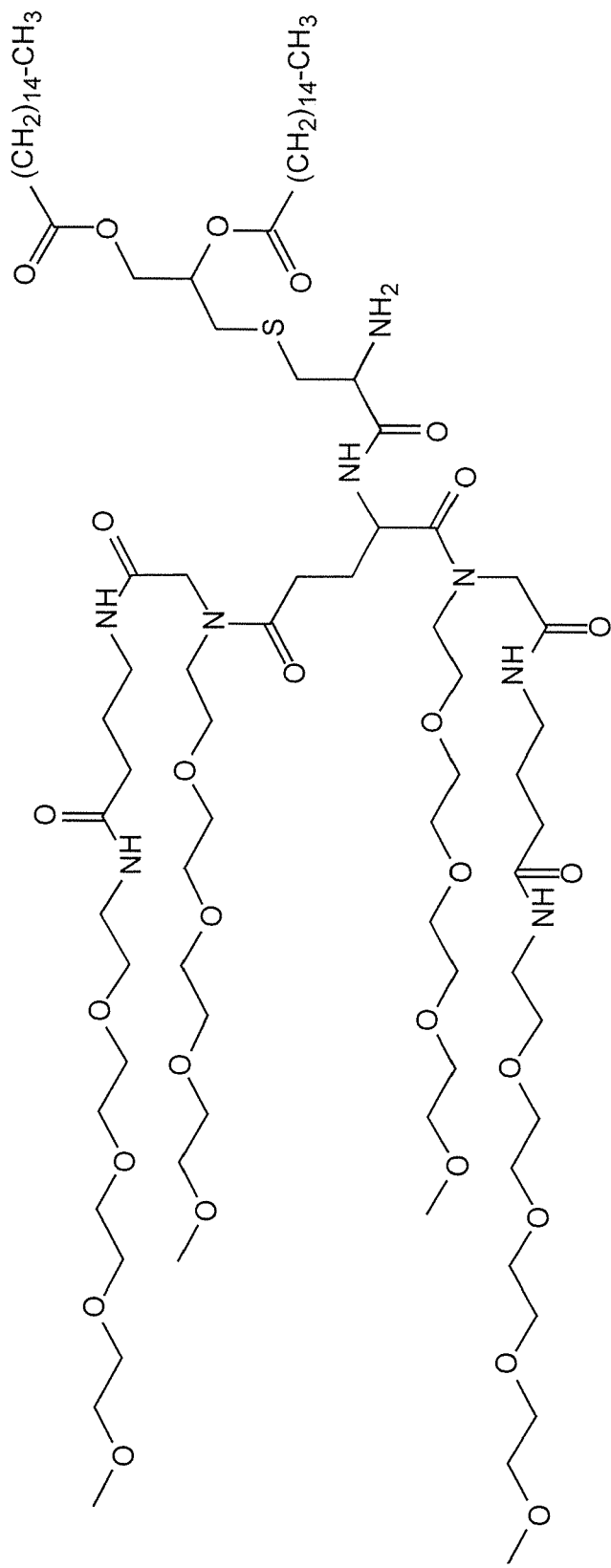
FIG. 11.
Figure 12:
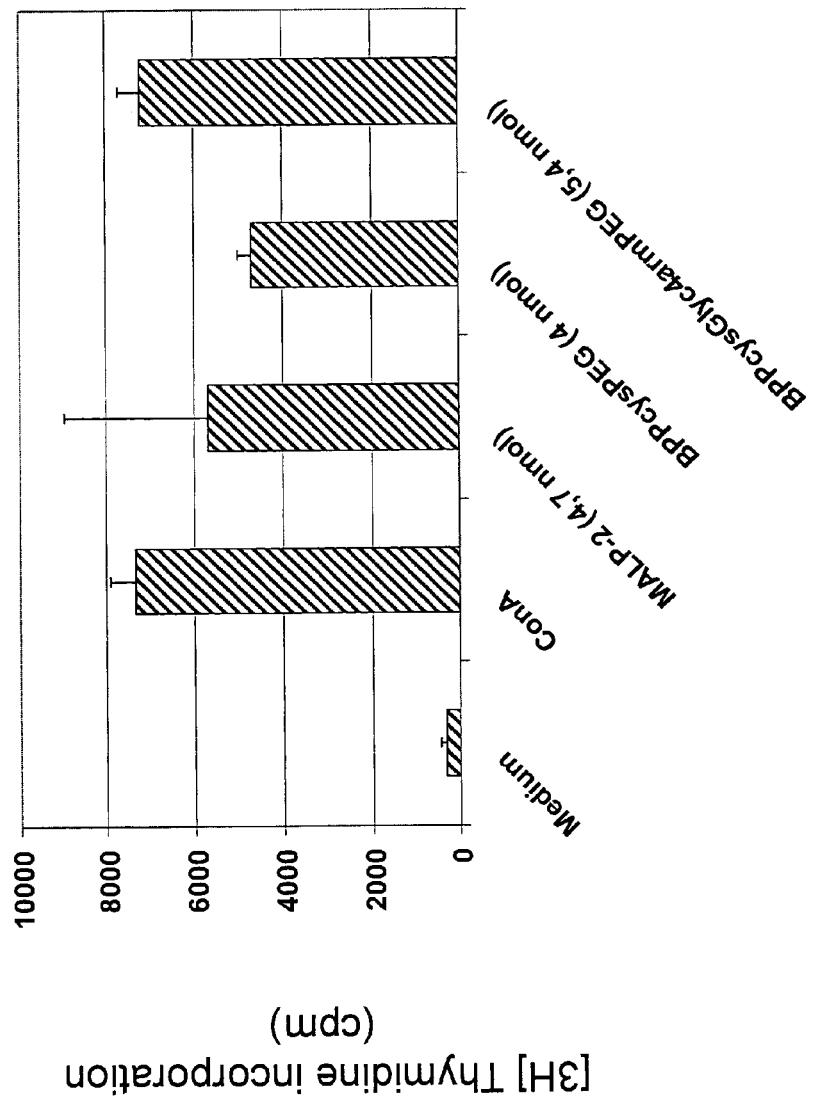
FIG. 12.

An increment in the number of splenic IFNγ producing cells was observed in animals immunized with the 1-Gal and BPPcysGlyc4armPEG or BPPcysAda (FIGS. 9A and 9B), in response to restimulation with a peptide encompassing the MHC class 1-restricted immunodominant epitope from β-Galactosidase. Furthermore, an enhanced expression of splenic IL-2 and IL-4 producing cells was shown in mice immunized with the 1-Gal and BPPcysGlyc4armPEG or BPPcysAda by the i.n. and even by the s.c. route.

The invention claimed is:

1. A Bisacyloxypropylcysteine-conjugate according to formula 1:

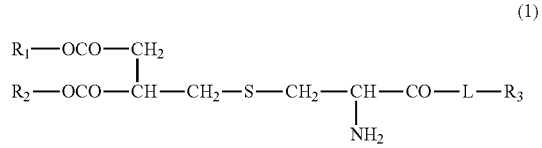

where
$R_1$ and $R_2$ can be identical or different and are acyl moieties;
L is a linker moiety selected from the group of NH, O, S or C(O)O;
$R_3$ is a covalently linked conjugate moiety comprising at least two polyalkylene glycol units of the formula:

$$X_1-[(CHR_4)_x-O]_n-(CHR_4)_y-$$

which may be identical or different;
$X_1$ is hydrogen or a hydrocarbon which may contain heteroatom(s);
$R_4$ is independently any one of hydrogen or straight or branched $C_1$-$C_6$ alkyl group, $OR_5$ or $CO$—$R_6$;
$R_5$ is independently any one of hydrogen or straight or branched $C_1$-$C_6$ alkyl group;
$R_4$ is independently any one of hydrogen, OH, $OR_5$ or $NR_7R_8$;
$R_7$ and $R_8$ are independently any one of hydrogen or hydrocarbon which may contain heteroatom(s) and which may form a ring;
n is an integer of 1 to 100;
x is independently an integer of 1 to 10; and
y is an integer of 0 to 10.

2. A conjugate according to claim 1, wherein each of the residues $R_1$ and $R_2$ is a $C_7$-$C_{25}$ acyl group.

3. A conjugate according to claim 1 wherein the acyl group is a straight, cyclic or branched $C_8$-$C_{22}$-alkyl, straight, cyclic or branched $C_8$-$C_{22}$-alkenyl, or straight, cyclic or branched $C_8$-$C_{22}$-alkynyl group which may optionally be substituted.

4. A conjugate according to claim 1, wherein the conjugate is a S-[2,3-bis(acyloxy)-(2S)-propyl]-L-cysteinylcarboxy-conjugate.

5. A conjugate according to claim 1, wherein the conjugate is a S-[2,3-bis(acyloxy)-(2R)-propyl]-L-cysteinylcarboxy-conjugate.

6. A conjugate according to claim 1, wherein in $R_3$ each of the at least two polyalkylene glycol units are composed of ethylene glycol, propylene glycol, and/or butylene glycol units or combinations thereof and n is an integer of from 3 to 50.

7. A conjugate according to claim 1, wherein $X_1$ in the at least two polyalkylene glycol units is independently a methoxy or ethoxy group.

8. A conjugate according to claim 1, wherein in $R_3$ each of the at least two polyalkylene glycol units includes methoxy-polyethylene glycol units wherein n is independently of from 3 to 10.

9. The conjugate according to claim 1 wherein the conjugate moiety is (S)-10-Amino-6,9,13,16-tetraoxo-N,N',8,14-tetrakis(3,6,9,12-tetraoxamidec-1-yl)-5,8,14,17-tetraaza-henicosane-1,21-diamide.

10. A conjugate according to claim 1, wherein the conjugate is the conjugate according to formula (2):

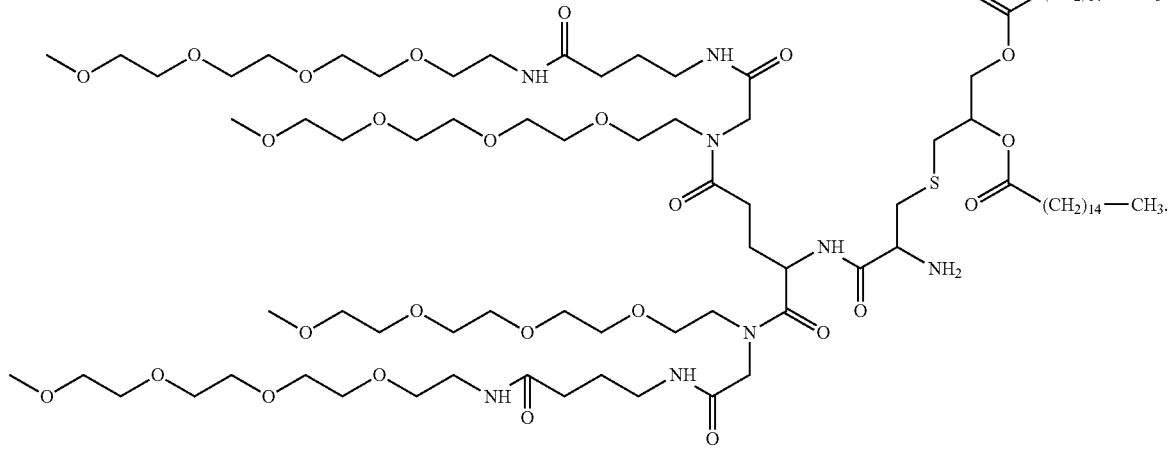

11. A pharmaceutical composition comprising a conjugate as defined claim 1 and a pharmaceutically acceptable carrier, diluent, preservative, adjuvants, immunomodulators or excipient.

12. A pharmaceutical composition comprising a compound or conjugate as defined in claim 1 as an adjuvant, at least one active ingredient and a pharmaceutically acceptable carrier, diluent, preservative, adjuvants other than the compounds or conjugates immunomodulators or excipient.

13. The pharmaceutical composition according to claim 12, wherein the pharmaceutical composition is a prophylactic and/or therapeutic vaccine.

14. The pharmaceutical composition according to claim 12 wherein the at least one active ingredient(s) comprises at least one or more different antigens in the form of peptides, proteins, polysaccharides, glycolipids or DNA encoding them and/or antigen delivery systems such as virosomes, physical particles, preferably microparticle, nanoparticle, liposome, ISCOM, copolymer and/or biological particle, preferably bacterial ghosts, virus-like particles (VLP), polyoma-like particles (PLP) or attenuated vaccines.

15. The pharmaceutical composition according to claim 14, wherein the at least one active ingredient is the one or more different antigens and the one or more different antigens are tumor antigen(s) or antigen(s) derived from infectious agents to prevent or treat infectious diseases, septic shock, cancer, tumours, autoimmune diseases, allergies, or chronic or acute inflammatory processes.

16. The pharmaceutical composition according to claim 12 wherein the at least one active ingredient is one or more antigens and wherein the adjuvant is admixed or co-formulated with the one or more antigens.

17. The pharmaceutical composition according claim 12, further comprising one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

18. A pharmaceutical composition according claim 12, wherein the at least one active ingredient includes one or more antigens and wherein at least one of the one or more antigens or the adjuvant is associated and/or incorporated and/or coated to a physical particle.

19. A pharmaceutical composition according to claim 12 provided in a formulation suitable for mucosal administration, in particular, for intranasal, intra NALT, oral, intrarectal, intrapulmonary, intrabronchial, intrathecal, conjunctival, intra-vaginal or intra-urethral administration, administration into the milk ducts of the breast or by inhalation.

20. A pharmaceutical composition according to claim 12 provided in a formulation suitable for parenteral administration, in particular, in subcutaneous, transcutaneous (topical vaccination), intravenous, intradermal or intramuscular administration.

21. A pharmaceutical composition according to claim 12 as a combined composition for simultaneous, separate or sequential use in preventing or treating infectious diseases, cancers, tumours, autoimmune diseases or allergies, or chronic or acute inflammatory processes or to control fertility in human or animal populations.

22. A pharmaceutical composition according claim 12, wherein the at least one active ingredient includes one or more antigens and wherein at least one of the one or more antigens or the adjuvant is associated and/or incorporated and/or coated to a physical particle selected from the group consisting of microparticle, nanoparticle, liposome, ISCOM, copolymer and/or biological particle.

23. The pharmaceutical composition according to claim 22 wherein said physical particle is a biological particle, and wherein said biological particle is selected from the group consisting of bacterial ghosts, virosomes, virus-like particles (VLP), polyoma-like particles (PLP) or attenuated vaccines.

24. A kit comprising a compound according to claim 1 together with instructions for use of said compound.

25. The kit according to claim 24 comprising the compound as an adjuvant and an antigenic structure and, optionally, a pharmaceutically acceptable carrier, diluent, preservative, adjuvants other than the conjugates immunomodulators or excipient.

26. A pharmaceutical composition containing a conjugate according to claim 1 as immunomodulator for preventing or treating infectious diseases, cancers, tumours, autoimmune diseases or allergies, or chronic or acute inflammatory processes or to control fertility in human or animal populations.

27. A conjugate according to claim 1, wherein the conjugate is a S-[2,3-bis(palmitoyloxy)-(2S)-propyl]-L-cysteinyl-carboxy-conjugate.

28. A conjugate according to claim 1, wherein the conjugate is a S-[2,3-bis(palmitoyloxy)-(2R)-propyl]-L-cysteinyl-carboxy-conjugate.

29. A conjugate according to claim 1, wherein in $R_3$ each of the at least two polyalkylene glycol units includes methoxy-polyethylene glycol units wherein n is independently of from 3 to 4.

* * * * *

UNITED STATES PATENT AND TRADEMARK OFFICE
CERTIFICATE OF CORRECTION

PATENT NO. : 8,119,689 B2
APPLICATION NO. : 12/093865
DATED : February 21, 2012
INVENTOR(S) : Thomas Ebensen, Michael Morr and Carlos Guzman It is certified that error appears in the above-identified patent and that said Letters Patent is hereby corrected as shown below:

In the Claims

At Column 23, Claim 1, Lines 13 to 17 to read as follows:

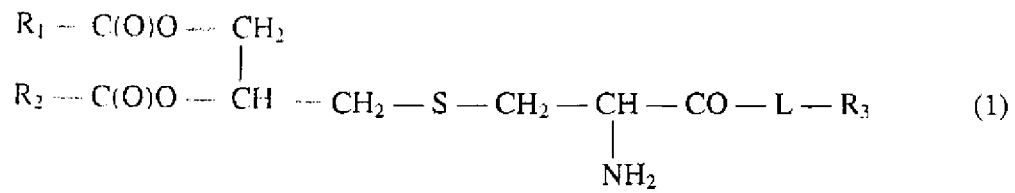 (1)

Signed and Sealed this
Thirteenth Day of May, 2014

Michelle K. Lee
*Deputy Director of the United States Patent and Trademark Office*